(12) United States Patent
Roth et al.

(10) Patent No.: US 7,842,277 B2
(45) Date of Patent: Nov. 30, 2010

(54) MOLECULAR SIEVE COMPOSITION, A METHOD OF MAKING AND A PROCESS OF USING THE SAME

(75) Inventors: Wieslaw J. Roth, Sewell, NJ (US); Machteld M. Mertens, Boortmeerbeek (BE); Els C. De Clerck, Aarschot (BE); Ivy D. Johnson, Lawrenceville, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 618 days.

(21) Appl. No.: 11/827,953

(22) Filed: Jul. 13, 2007

(65) Prior Publication Data

US 2008/0045768 A1    Feb. 21, 2008

Related U.S. Application Data

(60) Provisional application No. 60/834,030, filed on Jul. 28, 2006, provisional application No. 60/834,001, filed on Jul. 28, 2006, provisional application No. 60/834,032, filed on Jul. 28, 2006, provisional application No. 60/834,031, filed on Jul. 28, 2006, provisional application No. 60/926,204, filed on Apr. 25, 2007.

(51) Int. Cl.
*C01B 39/48* (2006.01)
*C01B 39/46* (2006.01)
*C01B 39/04* (2006.01)

(52) U.S. Cl. ........... 423/718; 423/704; 423/708; 560/352; 588/54; 588/579; 588/700; 585/258; 585/407; 585/467; 585/475; 585/654

(58) Field of Classification Search ............. 423/708, 423/718, 704; 208/27, 46, 59, 146; 568/54, 568/579, 700; 560/352; 585/258, 407, 467, 585/475, 654
See application file for complete search history.

(56) References Cited

U.S. PATENT DOCUMENTS

| 4,439,409 A | 3/1984 | Puppe et al. |
| 4,826,667 A | 5/1989 | Zones et al. |
| 4,954,325 A | 9/1990 | Rubin et al. |
| 5,236,575 A | 8/1993 | Bennett et al. |

(Continued)

FOREIGN PATENT DOCUMENTS

WO    WO 2005/118476    12/2005

(Continued)

OTHER PUBLICATIONS

Lee et al, Microporous and Macroporous Materials, vol. 68 (2004), pp. 97-104.*

(Continued)

*Primary Examiner*—David M Brunsman
(74) *Attorney, Agent, or Firm*—D. M. Tyus; X. Feng

(57) ABSTRACT

This disclosure relates to a crystalline MCM-22 family molecular sieve composition having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11. Angstroms, wherein the peak intensity of the d-spacing maximum between 12.57 to about 14.17 Angstroms is less than 90% of the peak intensity of the d-spacing maximum at 12.33±0.23 Angstroms. This disclosure also relates to methods of making the crystalline MCM-22 family molecular sieve composition.

35 Claims, 11 Drawing Sheets

U.S. PATENT DOCUMENTS

| | | |
|---|---|---|
| 5,250,277 A | 10/1993 | Kresge et al. |
| 5,362,697 A | 11/1994 | Fung et al. |
| 6,077,498 A | 6/2000 | Diaz Cabanas et al. |

FOREIGN PATENT DOCUMENTS

| | | |
|---|---|---|
| WO | WO 2007/094937 | 8/2007 |
| WO | WO 2007/094938 | 8/2007 |

OTHER PUBLICATIONS

Chem. Lett. vol. 32, No. 6, p. 542-543 (2003) by S. H. Lee, C. H. Shin, and S. B Hong and Microporous and Mesoporous Materials, vol. 68, p. 97-104 (2004) by S. H. Lee, C. H. Shin, D. K. Yang, S. D. Ahn, I. S. Nam and S. B Hong.

Atlas of Zeolite Framework Types, eds. W. H. Meier, D. H. Olson and Ch. Baerlocher, Elsevier, Fifth Edition, 2001.

U.S. Appl. No. 60/834,030, filed Jul. 28, 2006, Inventor: Wieslaw J.Roth, et al., entitled, Molecular Sieve Composition (EMM-10-P).

U.S. Appl. No. 60/834,001, filed Jul. 28, 2006, Inventor: Wieslaw J.Roth, et al., entitled, Its Method of Making Molecular Sieve Composition (EMM-10-P).

U.S. Appl. No. 60/834,032, filed Jul. 28, 2006, Inventor: Wieslaw J.Roth, et al., entitled, Molecular Sieve Composition (EMM-10).

U.S. Appl. No. 60/834,031, filed Jul. 28, 2006, Inventor: Wieslaw J.Roth, et al., entitled Its Method of Making Molecular Sieve Composition (EMM-10).

\* cited by examiner

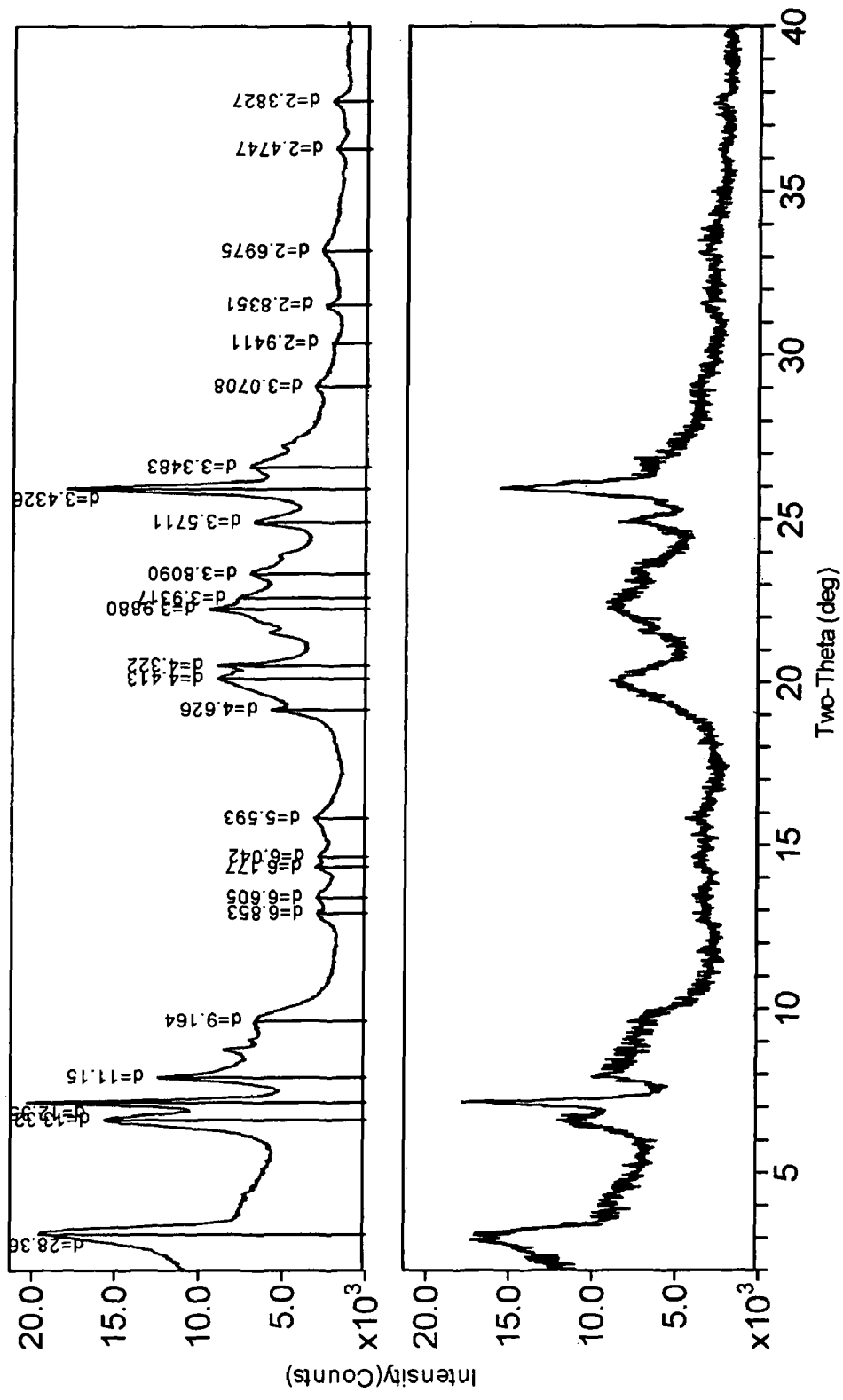
Figure 1a (top): XRD of Example 1 (80 hours); Figure 1b (bottom): XRD of Example 1 (92 hours)

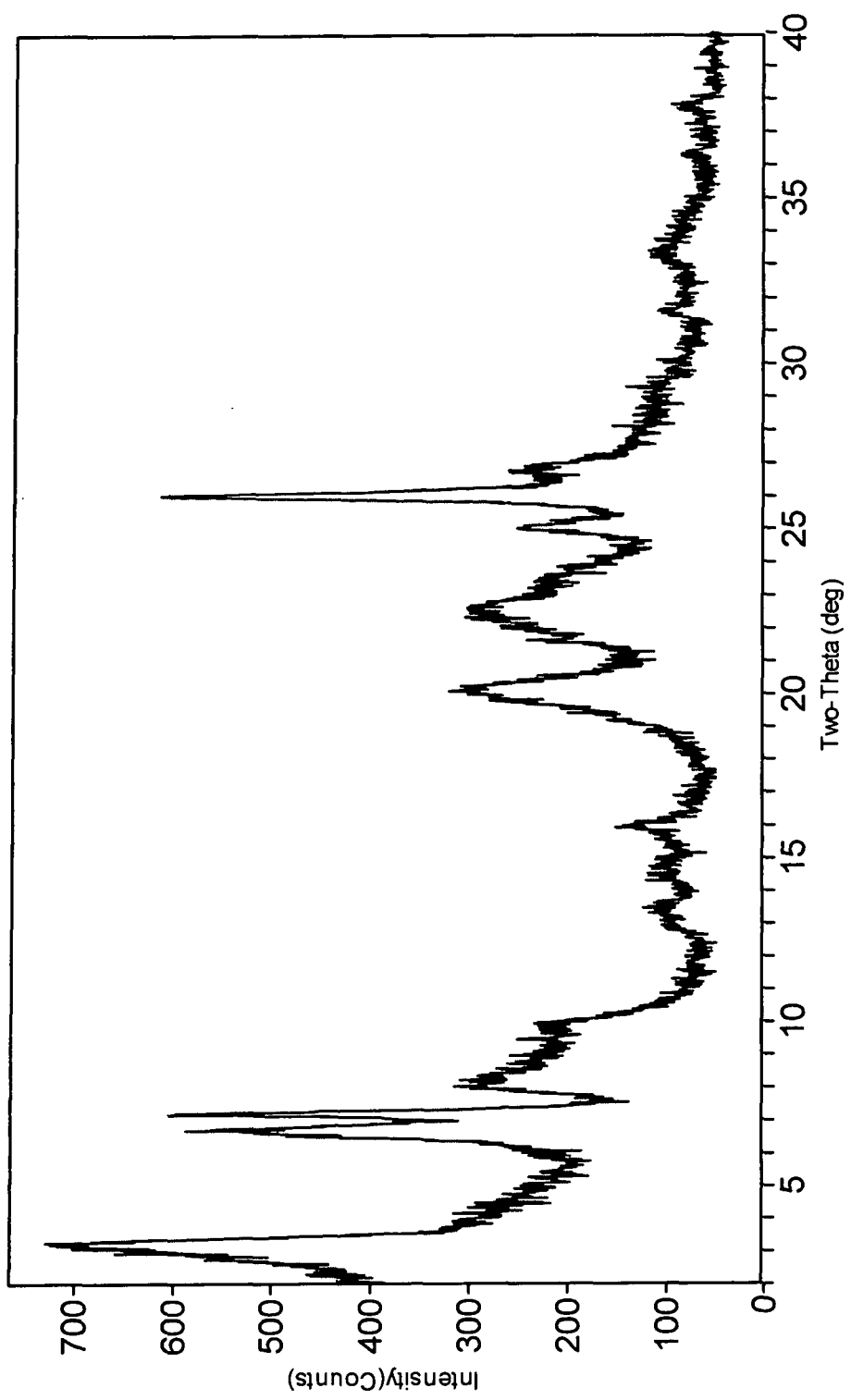
Figure 2: XRD of Example 1A

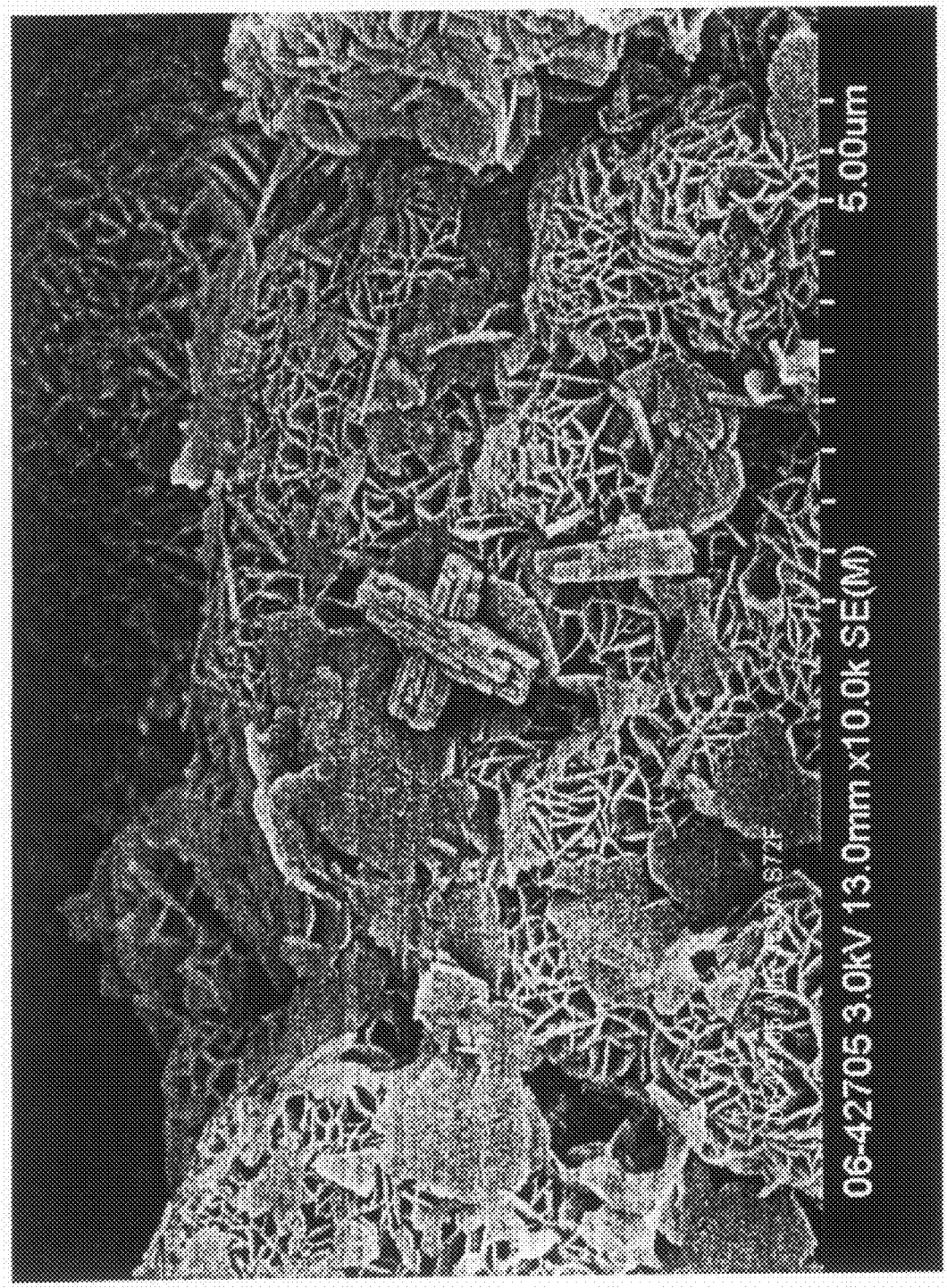
Figure 3: SEM of Example 1A

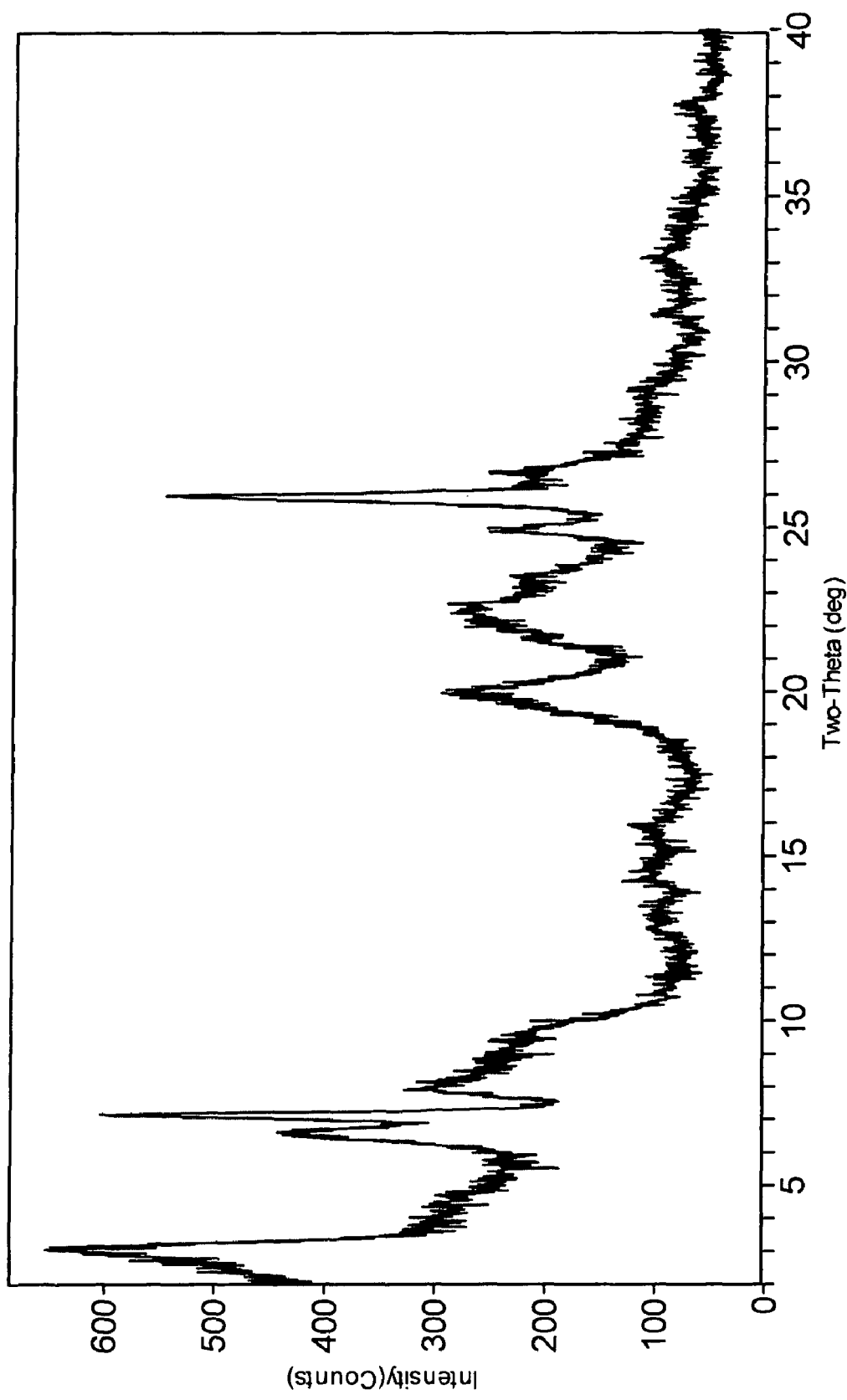
Figure 4: XRD of Example 2

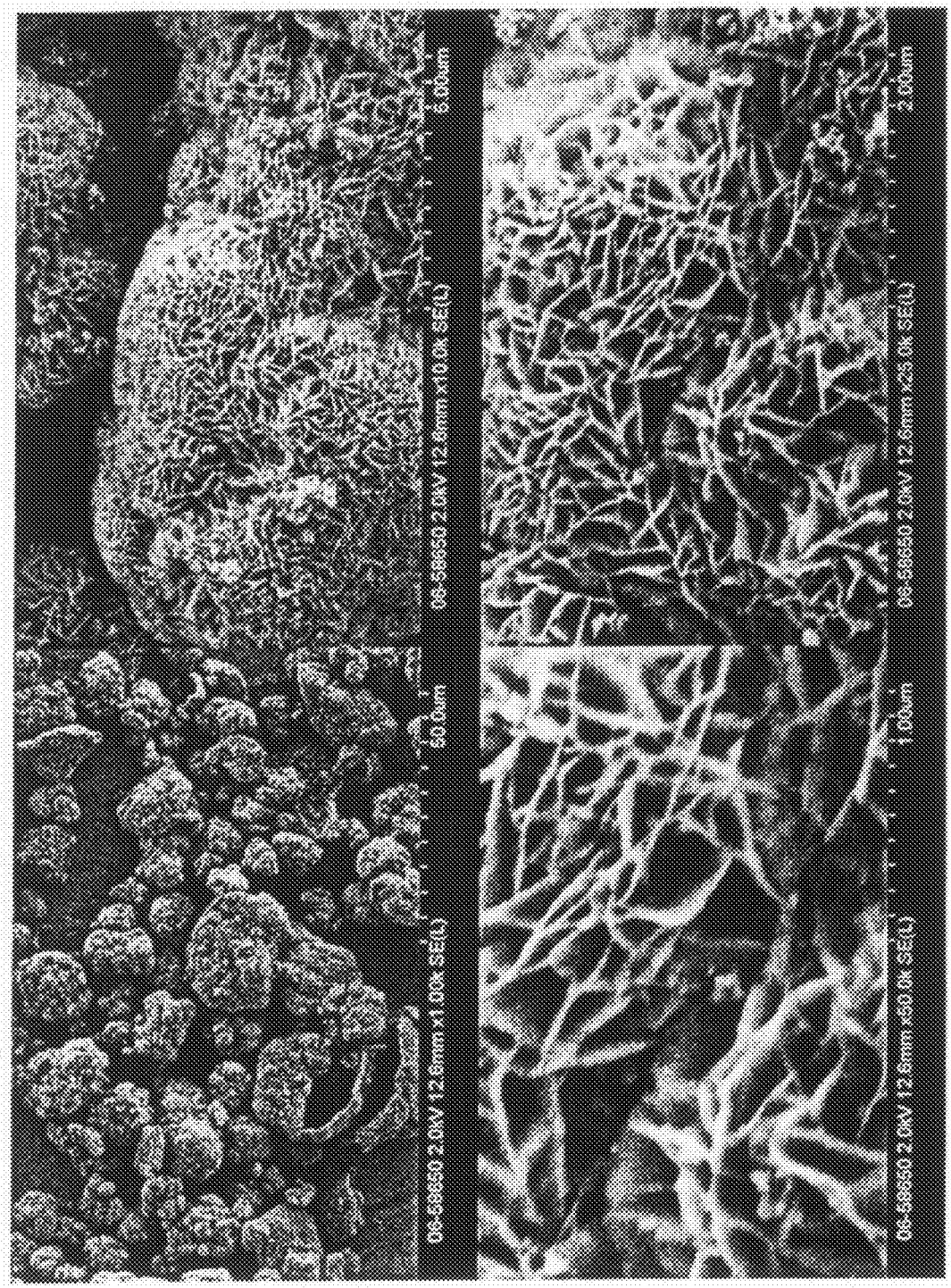
Figure 5a, b, c, and d: SEM of Example 2 with different resolutions:

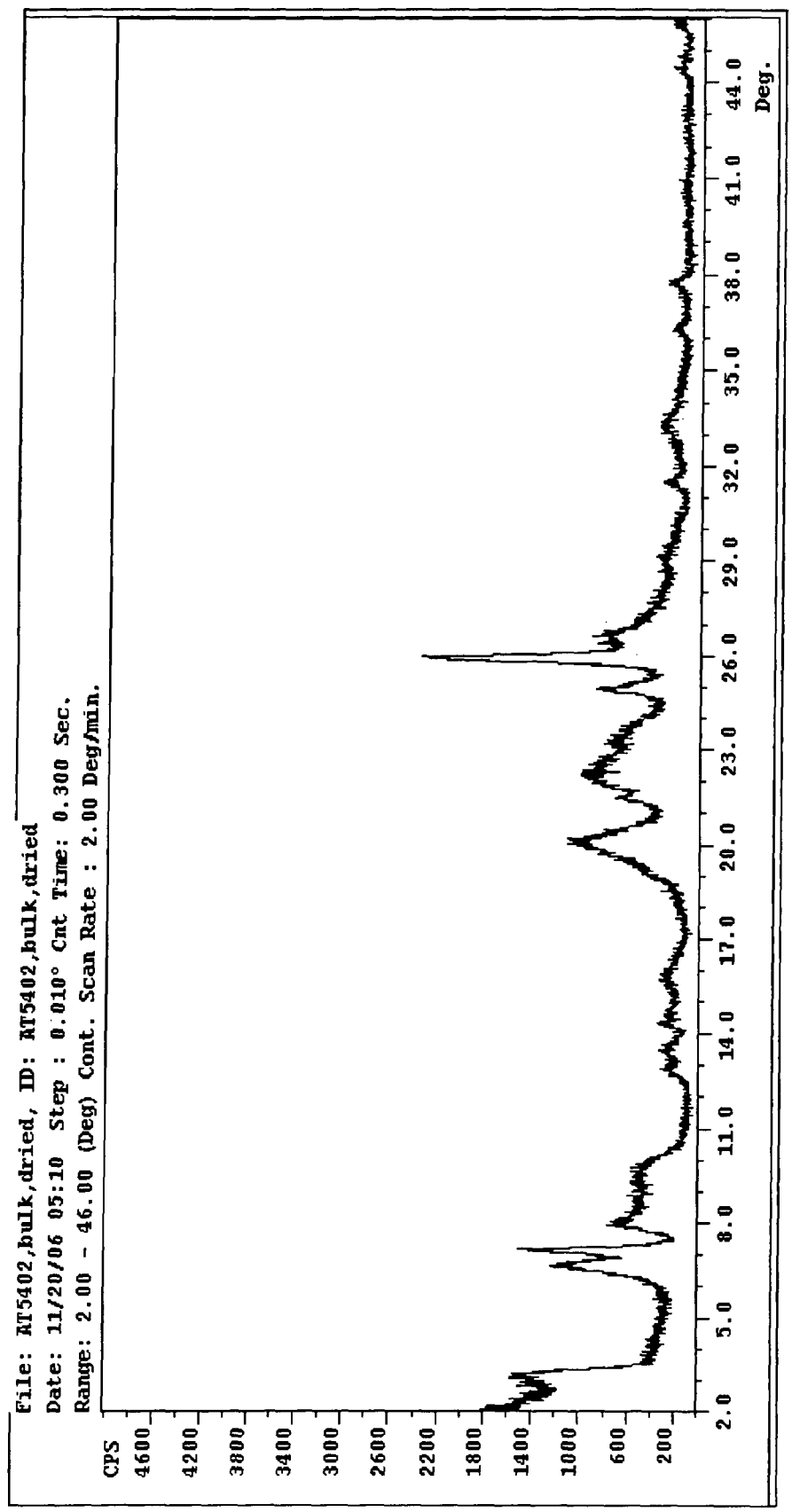
Figure 6: XRD of Example 3: Ge-free containing crystals

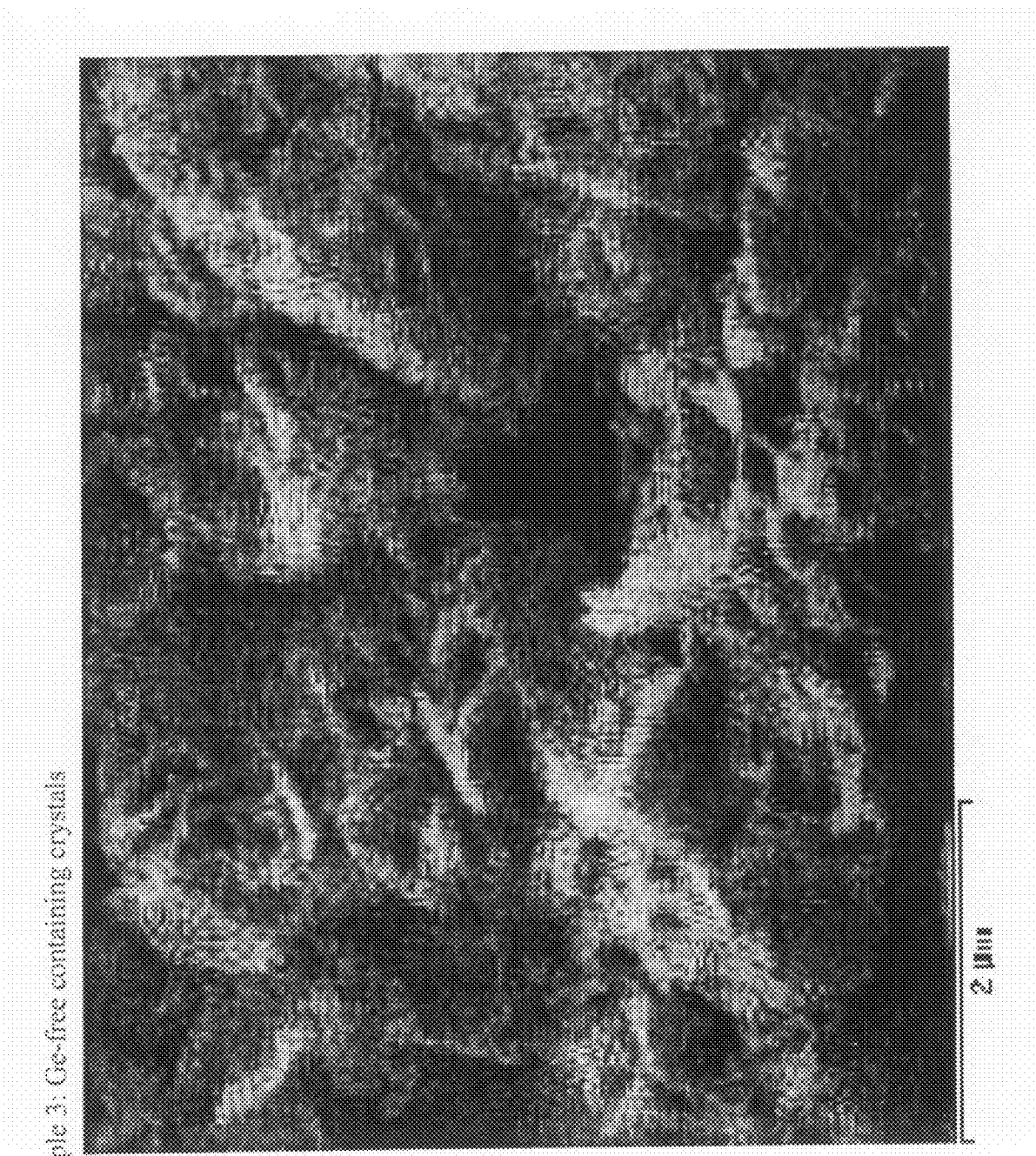
Figure 7: SEM of Example 3: Ge-free containing crystals

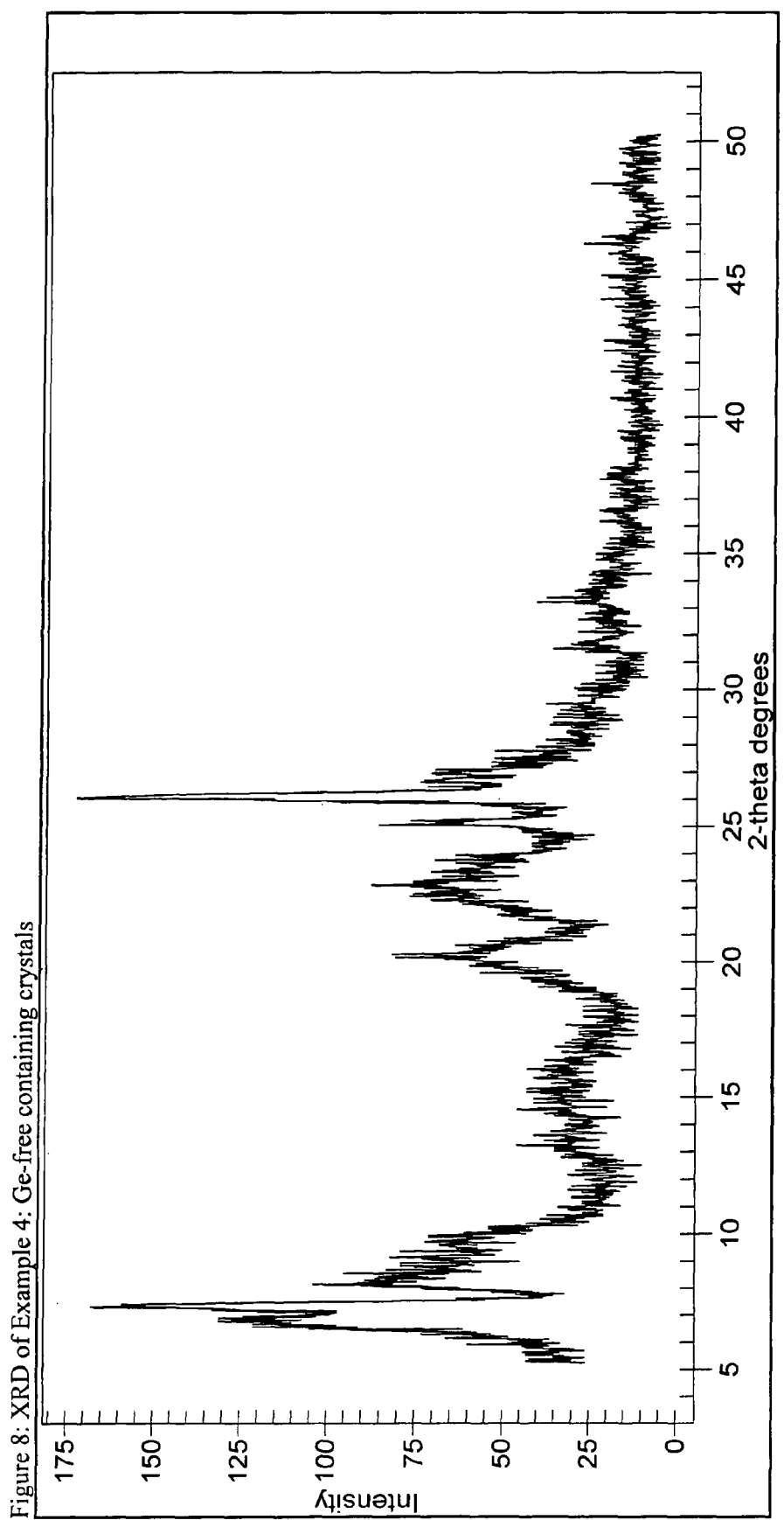
Figure 8: XRD of Example 4: Ge-free containing crystals

Figure 9: SEM of Example 4, Ge-free containing crystals

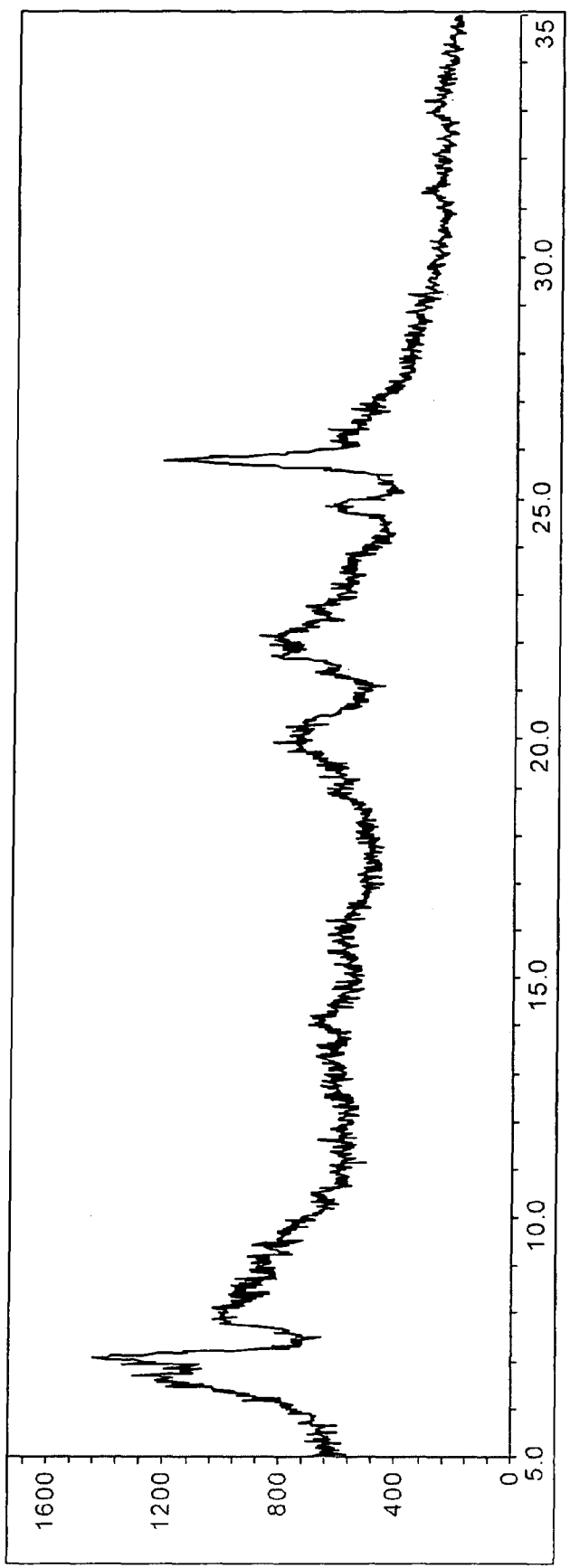
Figure 10: XRD of Example 5: Ge/Al containing crystals

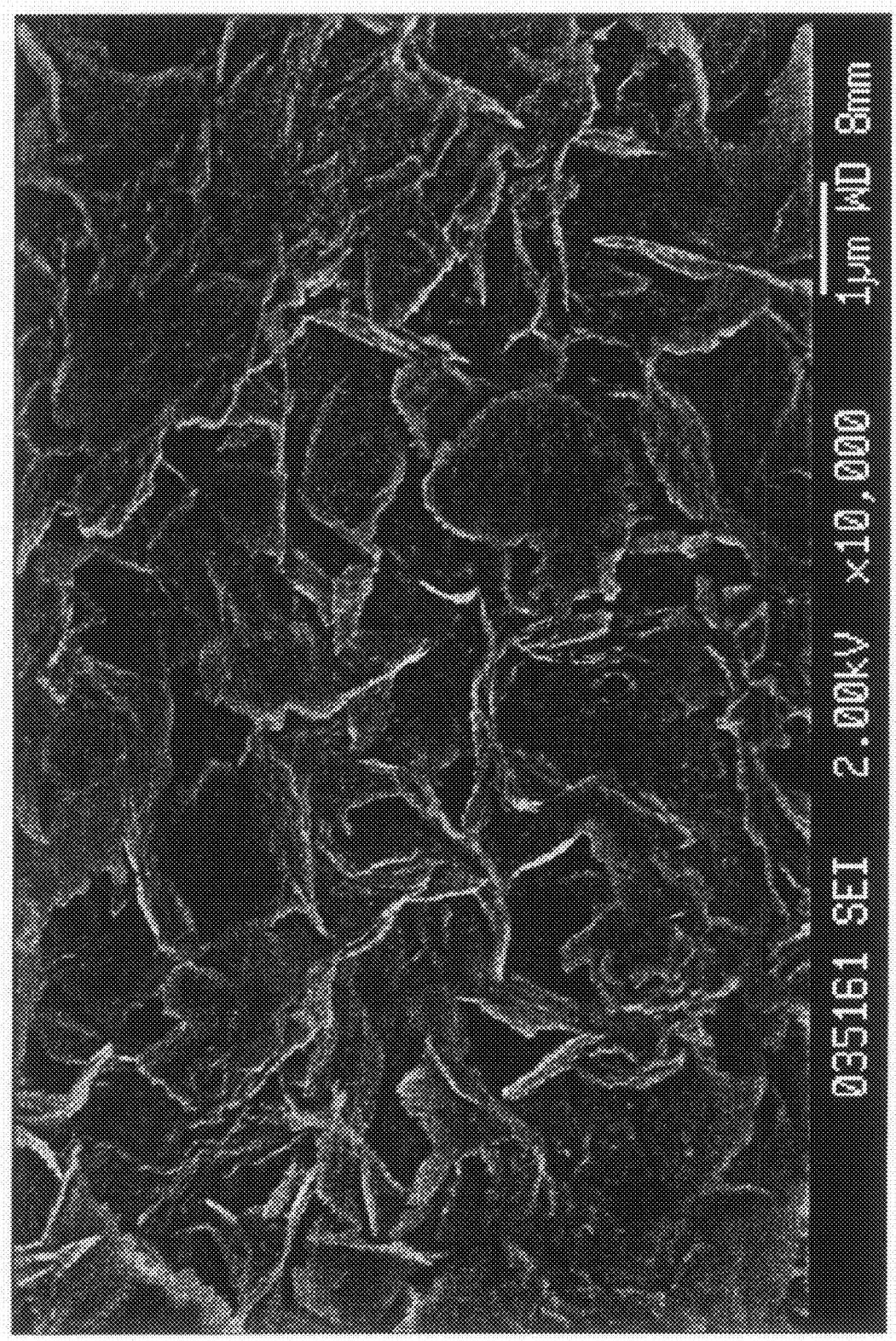
Figure 11: SEM of Example 5: Ge/Al containing crystals

MOLECULAR SIEVE COMPOSITION, A METHOD OF MAKING AND A PROCESS OF USING THE SAME

CROSS REFERENCE TO RELATED APPLICATIONS

This application claims priority to Provisional Application Nos. 60/834,030, 60/834,001, 60/834,032 and 60/834,031 filed Jul. 28, 2006 and claims the benefit of Provisional Application No. 60/926,204 filed Apr. 25, 2007, the entire disclosures of which are incorporated by reference in their entireties.

FIELD OF THE INVENTION

The present disclosure relates to a novel molecular sieve composition, a method of making and a process of using the same. In particular, this disclosure relates to a novel molecular sieve composition which is an EMM-10 or MCM-22 type material having low angle features of MCM-22-P and MCM-56.

BACKGROUND OF THIS DISCLOSURE

Molecular sieve materials, both natural and synthetic, have been demonstrated in the past to have catalytic properties for various types of hydrocarbon conversion. Molecular sieves that find application in catalysis include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Framework Types", eds. W. H. Meier, D. H. Olson and Ch. Baerlocher, Elsevier, Fifth Edition, 2001, which is hereby incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

U.S. Pat. No. 4,439,409 refers to a crystalline molecular sieve composition of matter named PSH-3 and its synthesis from a reaction mixture for hydrothermal reaction containing hexamethyleneimine, an organic compound which acts as directing agent for synthesis of the MCM-56 (U.S. Pat. No. 5,362,697). Hexamethyleneimine is also taught for use in synthesis of crystalline molecular sieves MCM-22 (U.S. Pat. No. 4,954,325) and MCM-49 (U.S. Pat. No. 5,236,575). A molecular sieve composition of matter referred to as zeolite SSZ-25 (U.S. Pat. No. 4,826,667) is synthesized from a reaction mixture for hydrothermal reaction containing an adamantane quaternary ammonium ion. U.S. Pat. No. 6,077,498 refers to a crystalline molecular sieve composition of matter named ITQ-1 and its synthesis from a reaction mixture for hydrothermal reaction containing one or a plurality of organic additives.

Chem. Lett. Vol. 32, No. 6, page 542-543 (2003) by S. H. Lee, C. H. Shin, and S. B Hong and Microporous and Mesoporous Materials, Vol. 68, page 97-104 (2004) by S. H. Lee, C. H. Shin, D. K. Yang, S. D. Ahn, I. S. Nam and S. B Hong reported a MCM-22 molecular sieve synthesized by crystallizing reaction mixture for hydrothermal reactions prepared from water, Me$_6$-diquat-5 dibromide, Ludox HS-40, aluminum nitrate non-hydrate, and 50 wt % sodium hydroxide solution. The mixtures had a molar composition as shown in Table I. The mixtures were crystallized under crystallization conditions (as shown in Table I) and characterized as pure phase MCM-22 with a crystal size of about 0.5×0.05 μm (micro plates morphology).

TABLE I

| | Chem. Lett. Vol. 32, No. 6, page 542-543 (2003) | Microporous and Mesoporous Materials, Vol. 68, page 97-104 (2004) | |
|---|---|---|---|
| Molar composition of the mixture | | | |
| SiO$_2$/Al$_2$O$_3$ | 60 | 30 | 60 |
| H$_2$O/SiO$_2$ | 40 | 40 | 40 |
| OH$^-$/SiO$_2$* | 0.63 | 0.4 | 0.5 |
| OH$^-$/SiO$_2$** | 0.73 | 0.6 | 0.6 |
| Na$^+$/SiO$_2$ | 0.73 | 0.6 | 0.6 |
| R/SiO$_2$ | 0.15 | 0.1 | 0.1 |
| Crystallization conditions | | | |
| Temperature (° C.) | | 160 | |
| Stirring speed (RPM) | | 100 | |
| Time (hr) | | 168 | |
| Product Characterization | | | |
| XRD Result | | Pure Phase MCM-22 | |
| SiO$_2$/Al$_2$O$_3$ (molar ratio) | 38 | | |
| BET area (m$^2$/g) | 438 | | |
| Crystal size | 0.5 × 0.05 μm | | |
| Morphology | Platelet | | Platelet |

*The OH$^-$/SiO$_2$ of this row is calculated with correction of aluminum source, wherein Al(NO$_3$)$_3$ was used in both papers.
**The OH$^-$/SiO$_2$ of this row is calculated without correction of aluminum source.

Provisional Patent Application No. 60/834,030 discloses a crystalline molecular sieve (EMM-10-P) having, in its as-synthesized form, an X-ray diffraction pattern including d-spacing maxima at 13.18±0.25 and 12.33±0.23 Angstroms, wherein the peak intensity of the d-spacing maximum at 13.18±0.25 Angstroms is at least as great as 90% of the peak intensity of the d-spacing maximum at 12.33±0.23 Angstroms.

Provisional Patent Application No. 60/834,001 discloses a method of making a crystalline molecular sieve (EMM-10-P), the method comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), said mixture having the following molar ratio:

Y:X$_2$=10 to infinity

H$_2$O:Y=1 to 10000

OH$^-$:Y=0.001 to 0.59

M$^+$:Y=0.001 to 2

R:Y=0.001 to 2 wherein M is an alkali metal and R is at least one N,N,N,N'N'N'-hexamethyl-1,5-pentanediaminium salt (Me$_6$-diquat-5 salt(s)); and (b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours.

Provisional Patent Application No. 60/834,032 discloses a crystalline molecular sieve (EMM-10), in its ammonium exchanged form or in its calcined form, comprising unit cells with MWW topology, said crystalline molecular sieve is characterized by diffraction streaking from the unit cell arrangement in the c direction. The crystalline molecular sieve is further characterized by the arced hk0 patterns of electron diffraction pattern. The crystalline molecular sieve is further characterized by the unit cells streaking along c direction.

Provisional Patent Application No. 60/834,031 discloses a method of making a crystalline molecular sieve (EMM-10), the method comprising the steps of:

(a) providing a mixture comprising at least one source of at least one tetravalent element (Y), at least one source of at least one trivalent element (X), at least one source of at least one alkali or alkali earth metal element, at least one directing-agent (R), and water, said mixture having the following molar composition:

Y:X$_2$=10 to infinity

H$_2$O:Y=1 to 10000

OH$^-$:Y=0.001 to 0.59

M$^+$:Y=0.001 to 2

R:Y=0.001 to 2 wherein M is an alkali metal and R is at least one N,N,N,N'N'N'-hexamethyl-1,5-pentanediaminium salt (Me$_6$-diquat-5 salt(s)); and (b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours;

(c) recovering the crystalline molecular sieve; and (d) ion-exchanging the crystalline molecular sieve with ammonium nitrate solution.

It is known that crystal morphology, size and aggregation/agglomeration, or new x-ray diffraction can affect catalyst behavior, especially regarding catalyst activity and stability. There is, therefore, a need for novel crystalline molecular sieve compositions and method of making such novel crystalline molecular sieve compositions.

SUMMARY OF THIS DISCLOSURE

In some embodiments, this disclosure relates to a crystalline MCM-22 family molecular sieve having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11. Angstroms, wherein the peak intensity of the d-spacing maximum between 12.57 to about 14.17 Angstroms is less than 90% of the peak intensity of the d-spacing maximum at 12.33±0.23 Angstroms.

In other embodiments, this disclosure relates to a method of making crystalline molecular sieve recited in any preceding claim, comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:

Y:X$_2$=10 to infinity

H$_2$O:Y=1 to 10000

OH$^-$:Y without trivalent element source correction=0.001 to 0.59, and/or OH$^-$:Y (with trivalent element source correction)=0.001 to 0.39

M$^+$:Y=0.001 to 2

R:Y=0.001 to 2 wherein M is an alkali metal and R is at least one N,N,N,N'N'N'-hexamethyl-1,5-pentanediaminium salt(s), N,N,N,N'N'N'-hexamethyl-1,6-hexanediaminium salt(s), or any combination thereof, wherein said OH$^-$:Y is calculated; and (b) submitting the mixture at crystallization conditions to form a product comprising the desired crystalline molecular sieve, wherein the crystallization conditions comprise a temperature in the range of from 100° C. to 250° C., a stirring speed of ranging from at least 150 RPM to less than 5000 RPM, and a crystallization time from about 1 hour to 400 hours; and (c) recovering the crystalline molecular sieve.

In yet other embodiments, this disclosure relates to a method of manufacturing a crystalline molecular sieve, the method comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:

Y:X$_2$=10 to infinity

H$_2$O:Y=1 to 10000

OH$^-$:Y without trivalent element source correction=0.74 to 2 and/or OH$^-$:Y with trivalent element source correction=0.64 to 2

M$^+$:Y=0.001 to 2

R:Y=0.001 to 2 wherein M is an alkali metal and R is at least one N,N,N,N'N'N'-hexamethyl-1,5-pentanediaminium salt(s), N,N,N,N'N'N'-hexamethyl-1,6-hexanediaminium salt(s), or any combination thereof, wherein said OH$^-$:Y is calculated without trivalent element source correction; and (b) submitting the mixture at crystallization conditions to form a product comprising the desired crystalline molecular sieve, wherein the crystallization conditions comprise a temperature in the range of from 100° C. to 200° C., a stirring speed of ranging from at least 150 RPM to less than 5000 RPM, and a crystallization time from about 1 hour to 400 hours; and (c) recovering the crystalline molecular sieve.

In yet other embodiments, this disclosure relates to a method of manufacturing a crystalline molecular sieve, the method comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:

Y:$X_2$=10 to infinity
$H_2O$:Y=5 to 35
$OH^-$:Y=0.001 to 2
$M^+$:Y=0.001 to 2
R:Y=0.001 to 2
wherein M is an alkali metal and R is at least one N,N,N,N'N'N'-hexamethyl-1,5-pentanediaminium salt(s), N,N,N,N'N'N'-hexamethyl-1,6-hexanediaminium salt(s), or any combination thereof, wherein said $OH^-$:Y is calculated with or without trivalent element source correction; and (b) submitting the mixture at crystallization conditions to form a product comprising the desired crystalline molecular sieve, wherein the crystallization conditions comprise a temperature in the range of from 100° C. to 200° C., a stirring speed of ranging from at least 150 RPM to less than 5000 RPM, and a crystallization time from about 1 hour to 400 hours; and (c) recovering the crystalline molecular sieve.

In yet other embodiments, this disclosure relates to a method of manufacturing a crystalline molecular sieve, the method comprising the steps of:

(a) providing a mixture comprising at least one source of at least one tetravalent element (Y), at least one source of at least one alkali or alkali earth metal element, at least one directing-agent (R), water, at least one seed, and optionally at least one source of at least one trivalent element (X), the mixture having the following molar ratio:

Y:$X_2$=10 to infinity
$H_2O$:Y=1 to 10000
$OH^-$:Y=0.001 to 2
$M^+$:Y=0.001 to 2
R:Y=0.001 to 2
wherein M is an alkali metal and R is at least one N,N,N,N'N'N'-hexamethyl-1,5-pentanediaminium salt(s), N,N,N,N'N'N'-hexamethyl-1,6-hexanediaminium salt(s), or any combination thereof, wherein said $OH^-$:Y is calculated with or without trivalent element source correction, wherein the seed has a concentration in the mixture ranging from about 0.01 to 10 wt % based on the weight of the tetravalent element oxide in the mixture; and (b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours; and (c) recovering the crystalline molecular sieve.

In yet other embodiments, this disclosure relates to a method of manufacturing a crystalline molecular sieve, the method comprising the steps of:

(a) providing a mixture comprising at least one source of at least one non-germanium tetravalent element (Y), at least one source of germanium (Ge), at least one directing-agent (R), water, and optionally at least one source of at least one trivalent element (X) and at least one source of at least one alkali or alkali earth metal element, the mixture having the following molar ratio:

(Ge+Y):$X_2$=10 to infinity
$H_2O$:Y=1 to 10000
$M^+$:Y=0 to 2
R:Y=0.001 to 2
wherein M is an alkali metal and R comprises at least one N,N,N,N'N'N'-hexamethyl-1,5-pentanediaminium salt(s), N,N,N,N'N'N'-hexamethyl-1,6-hexanediaminium salt(s), or any combination thereof; and (b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours; and (c) recovering the crystalline molecular sieve.

In some embodiments, this disclosure relates to an MCM-22 family molecular sieve made by methods of this disclosure.

In other embodiments, this disclosure relates to a process for hydrocarbon conversion, comprising the step of contacting a hydrocarbon feedstock with the crystalline molecular sieve made by the method of in any one of claims 7-30 or the crystalline molecular sieve of claims 1-6, under conversion conditions to form a product.

These and other facets of the present invention shall become apparent from the following detailed description, Figures, and appended claims.

BRIEF DESCRIPTION OF THE FIGURES

FIG. 1a shows the XRD of the as-synthesized product of Example 1 at 80 hours.

FIG. 1b shows the XRD of the as-synthesized product of Example 1 at 92 hours.

FIG. 2 shows the XRD of the as-synthesized product of Example 1A.

FIG. 3 shows SEM for Example 1A.

FIG. 4 shows the XRD of the as-synthesized product of Example 2.

FIG. 5 shows the SEM of the as-synthesized product of Example 2.

FIG. 6 shows the XRD of the as-synthesized product of Example 3.

FIG. 7 shows the SEM of the as-synthesized product of Example 3.

FIG. 8 shows the XRD of the as-synthesized product of Example 4.

FIG. 9 shows the SEM of the as-synthesized product of Example 4.

FIG. 10 shows the XRD of the as-synthesized product of Example 5.

FIG. 11 shows the SEM of the as-synthesized product of Example 5.

DETAILED DESCRIPTION

In some embodiments, this disclosure relates to a crystalline MCM-22 family molecular sieve having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11. Angstroms, wherein the peak intensity of the d-spacing maximum between 12.57 to about 14.17 Angstroms is less than 90% of the peak intensity of the d-spacing maximum at 12.33±0.23 Angstroms. In other embodiments, this disclosure relates to methods of making and processes of using the same.

Introduction

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "tabular habit" morphology as used herein means a tabular mineral having "parallel stacked thin platelike crystals." The term "platelet" morphology as used herein means thin platelike crystals.

The term "MCM-22 family material" (or "material of the MCM-22 family" or "molecular sieve of the MCM-22 family"), as used herein, includes:

(i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;

(ii) molecular sieves made from a common second degree building block, a 2-dimensional tiling of such MWW framework type unit cells, forming a "monolayer of one unit cell thickness", preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, or any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), UZM-8 (described in U.S. Pat. No. 6,756,030), and MCM-56 (described in U.S. Pat. No. 5,362,697). The entire contents of the patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, UZM-8, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

It will be understood by a person skilled in the art that the MCM-22 family material may contain impurities, such as amorphous materials; unit cells having non-MWW framework topologies (e.g., MFI, MTW); and/or other impurities (e.g., heavy metals and/or organic hydrocarbons). Typical examples of the non-MCM-22 family molecular sieve(s) co-existing with the MCM-22 family molecular sieve(s) of this disclosure are Kenyaite, EU-1, ZSM-50, ZSM-12, ZSM-48, ZSM-5, Ferrierite, Mordenite, Sodalite, and/or Analcine. Other examples of the non-MCM-22 family molecular sieve(s) co-existing with the MCM-22 family molecular sieve(s) of this disclosure are molecular sieves having framework type of EUO, MTW, FER, MOR, SOD, ANA, and/or MFI. The MCM-22 family materials of this disclosure are preferably substantially free of non-MCM-22 family material(s). The term "substantially free of non-MCM-22 family material(s)" used herein means the MCM-22 family material of this disclosure preferably contains a minor proportion (less than 50 wt %), preferably less than 20 wt %, of non-MCM-22 family materials ("impurities") in the MCM-22 family materials, which weight percent (wt %) values are based on the combined weight of impurities and pure phase MCM-22 family materials.

It is to be understood that throughout this detailed description, common characterization techniques were used to describe molecular sieve materials. These common techniques are included ascertaining:

(a) structure and the degree of crystallinity of the molecular sieve material by X-Ray Diffraction (XRD); and/or (b) morphology and crystal size of the molecular sieve material measured by the Scanning Electron Microscope (SEM); and/or (c) chemical composition by atomic absorption spectrometry and/or Inductively Coupled Plasma Mass Spectrometry (ICP-MS or ICPMS);
(d) adsorption capacities and surface area measured by nitrogen BET method; and/or
(e) catalytic activities and catalytic stabilities measured by the probing reactions.

X-Ray Powder Diffraction Pattern

The interplanar spacings, d's, were calculated in Angstrom units (Å), and the relative intensities of the lines, $I/I_o$, where the intensity of the strongest line above background, $I_o$, is counted as 100, were derived with the use of a profile fitting routine (or second derivative algorithm). The intensities are uncorrected for Lorentz and polarization effects. The relative intensities are given in terms of the symbols VS=very strong (greater than 60 to 100), S=strong (greater than 40 to 60), M=medium (greater than 20 to 40) and W=weak (0 to 20). It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-22 with similar materials, e.g., MCM-49, MCM-56, and PSH-3.

The interplanar spacings, d's, were considered broad if they exhibited peak width of about 1.5° or more at half height determined as 50% intensity value from the maximum to the baseline.

The term "XRD distinguishable peak" as used herein is defined as XRD peak with clearly defined peak maximum, which is at least two times of the average background noise level.

The term "non-discrete" peaks (also "unresolved" peaks) in XRD as used herein means peaks having a monotonic profile in-between them (successive points either consistently increasing (or staying even) or decreasing (or staying even) within noise).

The term "discrete" peaks (also "resolved" peaks) in XRD as used herein means XRD peak(s) which are not non-discrete (unresolved).

The crystalline molecular sieve composition of this disclosure may be characterized by an X-ray diffraction pattern of the as-synthesized crystalline molecular sieve including three peaks; (1) d-spacing maximum at 12.33±0.23 Angstroms; (2) d-spacing maximum between 14.17 and 12.57 Angstroms, (Table II); and (3) a non-discrete d-spacing maximum between 8.8 and 11.1 Angstroms, wherein the peak intensity of the d-spacing maximum between 14.17 and 12.57 Angstroms is less than 90% of the peak intensity of the d-spacing maximum at 12.33±0.23 Angstroms.

TABLE II

| Interplanar d-Spacing (Å) | Relative Intensity, $I/I_o \times 100$ |
|---|---|
| 14.17 > d > 12.57 | M-VS |
| 12.33 | M-VS |

The crystalline molecular sieve composition of this disclosure may be characterized by an X-ray diffraction pattern of the as-synthesized crystalline molecular sieve including d-spacing maxima of as-as listed in Table III or Table IV.

TABLE III

| Interplanar d-Spacing (Å) | Relative Intensity, $I/I_o \times 100$ |
|---|---|
| 14.17 > d > 12.57 | M-VS |
| 12.33 ± 0.23 | M-VS |
| 11.1 to 8.8 | W-S |
| 3.57 ± 0.06 | W-M |
| 3.43 ± 0.06 | M-VS |

TABLE IV

| Interplanar d-Spacing (Å) | Relative Intensity, $I/I_o \times 100$ |
|---|---|
| 14.17 > d > 12.57 | M-VS |
| 12.33 ± 0.23 | M-VS |
| 11.1 to 8.8 | W-S |
| 4.41 ± 0.1 | W-M, broad |
| 3.96 ± 0.08 | W-VS, broad |
| 3.57 ± 0.06 | W-M |
| 3.43 ± 0.06 | M-VS |

Comparing with similar materials (MCM-22, MCM-22-P, MCM-36, MCM-49, MCM-56, EMM-10-P and EMM-10), the composition of this disclosure has three key peaks which distinguish this composition from MCM-22, MCM-22-P, MCM-36, MCM-49, MCM-56, and EMM-10 as following:

(1) peak having a d-spacing maximum at 12.33±0.23 Angstroms: all materials, MCM-22, MCM-22-P, MCM-36, MCM-49, MCM-56, EMM-10-P, EMM-10, and the composition of this disclosure;

(2) peak having a d-spacing maximum between 14.17 and 12.57 Angstroms:
  (a) MCM-22, MCM-36, MCM-49, EMM-10 and MCM-56 do not have this peak,
  (b) MCM-22-P, EMM-10-P, and this material have this peak, however for EMM-10-P, this peak is at least 90% or even higher than the peak having d-spacing maximum at 12.33±0.23 Angstroms;

(3) non-discrete peak having a d-spacing maximum at between 8.66 to 11.3:
  (a) similar as MCM-56, MCM-36 and EMM-10-P
  (b) for all other materials, MCM-22, MCM-22-P, MCM-49 and EMM-10, this peak is a discrete peak, or partially resolved in the case of EMM-10.

The differences are summarized in the following Table V:

TABLE V

| | | Interplanar d-Spacing (Å) | | |
|---|---|---|---|---|
| | | 14.17-12.57 | 12.1-12.56 | 8.66-11.3 |
| Composition of this disclosure | XRD Peak position | | | |
| | Relative Intensity, $I/I_o \times 100$ | M-VS | M-VS | W-S (broad band) non discrete peak |

TABLE V-continued

| | | Interplanar d-Spacing (Å) | | | |
|---|---|---|---|---|---|
| MCM-22-P | XRD Peak position | 13.53 ± 0.2 | 12.36 ± 0.2 | 11.13 ± 0.2 | 9.15 ± 0.3 |
| | Relative Intensity, $I/I_o \times 100$ | M-VS | VS | M-S | M-S |
| MCM-22 | XRD Peak position | No distinct peak | 12.36 ± 0.2 | 11.03 ± 0.2 | 8.83 ± 0.14 |
| | Relative Intensity, $I/I_o \times 100$ | | VS | M-S | M-VS |
| MCM-36 | XRD Peak position | Above 32 | 12.38 ± 0.2 | 9.01-10.94 | |
| | Relative Intensity, $I/I_o \times 100$ | VS | M-S | W-S (broad band) non discrete peak | |
| MCM-49 | XRD Peak position | 13.15 ± 0.26 shoulder peak | 12.49 ± 0.24 | 11.19 ± 0.22 | 8.9 ± 0.2 |
| | Relative Intensity, $I/I_o \times 100$ | — | VS | M-S | W-S |
| MCM-56 | XRD Peak position | | 12.36 ± 0.2 | 9.2-11.1 | |
| | Relative Intensity, $I/I_o \times 100$ | | M-VS | W-S (broad band) non discrete peak | |

In some embodiments, the X-ray diffraction pattern of the crystalline molecular sieve of this disclosure further includes a d-spacing maximum at 28±1 Angstroms.

Scanning Electron Microscope (SEM)

The as-synthesized known MCM-22 crystalline material disclosed in Chem. Lett. Vol. 32, No. 6, page 542-543 (2003) by S. H. Lee, C. H. Shin, and S. B Hong is reported as having a particle size of about 0.5×0.05 µm and a platelet morphology.

The SEM image of a crystalline molecular sieve of this disclosure made by non-germanium and non-seeding preparations are demonstrated in FIG. 5. The crystalline molecular sieve as shown in FIG. 5 has a crystal morphology of 5-20 micron spherical (round, oval) aggregates of intergrown platelet crystals of less than 0.1 micron thickness. The SEM images of a crystalline molecular sieve of this disclosure made by germanium and/or seeding preparations are demonstrated in FIGS. 7, 9 and 11. The crystalline molecular sieves as shown in FIGS. 7, 9 and 11 have a crystal morphology of flakes with an estimated crystal size of the largest diameter less than 2 micron and an estimated thickness of about 100 nm.

Surface Areas and Adsorption Uptake

The overall surface area of a molecular sieve may be measured by the Brunauer-Emmett-Teller (BET) method using adsorption-desorption of nitrogen (temperature of liquid nitrogen, 77 K). The internal surface area may be calculated using t-plot of the Brunauer-Emmett-Teller (BET) measurement. The external surface area is calculated by subtracting the internal surface area from the overall surface area measured by the Brunauer-Emmett-Teller (BET) measurement.

The crystalline molecular sieve (after calcination) of this disclosure may be characterized by a preferred total surface area (sum of the external and the internal surface areas, as measured by the BET method) of greater than 450 m²/g, preferably greater than 475 m²/g, and more preferably greater than 500 m²/g.

In addition, the crystalline molecular sieve (after calcination) of this disclosure may be characterized by the ratio of the external surface area (as measured by the t-plot of BET method) over the total surface area of preferably less than 0.18.

Formulation of the Reaction Mixture for Hydrothermal Reactions

Synthetic molecular sieves are often prepared from aqueous reaction mixtures for hydrothermal reaction (synthesis mixture(s) or synthetic gel(s)) comprising sources of appropriate oxides. Organic directing agents may also be included in the reaction mixture for hydrothermal reaction for the purpose of influencing the production of a molecular sieve having the desired structure. The use of such directing agents is discussed in an article by Lok et al. entitled "The Role of Organic Molecules in Molecular Sieve Synthesis" appearing in Zeolites, Vol. 3, October, 1983, pp. 282-291.

After the components of the reaction mixture for hydrothermal reaction are properly mixed with one another, the reaction mixture for hydrothermal reaction is subjected to appropriate crystallization conditions. In some embodiments of this disclosure, such conditions usually involve heating of the reaction mixture for hydrothermal reaction to an elevated temperature and with stirring. Aging of the reaction mixture for hydrothermal reaction in a temperature ranging from 0° C. to 120° C. is also desirable in some instances.

The crystalline molecular sieve material of this disclosure may be prepared from a reaction mixture for hydrothermal reaction containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, in some preferred embodiments, the reaction mixture for hydrothermal reaction having a composition, in terms of mole ratios of oxides, within the following ranges in Table VI:

TABLE VI

| Reactants | Useful | Preferred |
|---|---|---|
| $YO_2/X_2O_3$ | 10 to infinity | 15-120 |
| $H_2O/YO_2$ | 1 to 10000 | 5-35 |
| $OH^-/YO_2$* | 0.001-0.39 | 0.1-0.35 |
| $OH^-/YO_2$** | 0.001-0.59 | 0.1-0.5 |
| $M/YO_2$ | 0.001-2 | 0.1-1 |

TABLE VI-continued

| Reactants | Useful | Preferred |
|---|---|---|
| R/YO$_2$ | 0.001-2 | 0.01-0.5 |
| Seed*** | 0-25 wt % | 1-5 wt % |
| R | Me$_6$-diquat-5 salt(s) | Me$_6$-diquat-5 salt(s) |

*The OH$^-$/YO$_2$ of this row is calculated with correction of trivalent element source.
**The OH$^-$/YO$_2$ of this row is calculated without correction of trivalent element source.
***The weight percent (wt %) of seed is based on the weight of the solid tetrahedral element oxide.

For these embodiments when reaction mixture for hydrothermal reaction having a composition as disclosed in Table VI, the OH$^-$:YO$_2$ molar ratio without correction of trivalent element source ranges from about 0.001 to about 0.59 and/or OH$^-$:YO$_2$ molar ratio with correction of trivalent element source ranges from about 0.001 to about 0.39.

The following OH$^-$:YO$_2$ molar ratios (without correction of trivalent element source) are useful lower OH$^-$:YO$_2$ molar ratio (without correction of trivalent element source) limits for these embodiments as disclosed in Table VI: 0.001, 0.002, 0.005, 0.01, 0.02, 0.05, 0.1, 0.2, 0.5, and 0.55. The following OH$^-$:YO$_2$ molar ratios (without correction of trivalent element source) are useful upper OH$^-$:YO$_2$ molar ratio (without correction of trivalent element source) limits for these embodiments as disclosed in Table VI: 0.59, 0.55, 0.51, 0.5, 0.4, 0.3, 0.2 and 0.1. The OH$^-$:YO$_2$ molar ratio (without correction of trivalent element source) ideally falls in a range between any one of the above-mentioned lower limits and any one of the above-mentioned upper limits, so long as the lower limit is less than or equal to the upper limit. The OH$^-$:YO$_2$ molar ratio (without correction of trivalent element source) may be present in an amount ranging from 0.001 to 0.59 in one embodiment, alternatively 0.01 to 0.5, alternatively 0.1 to 0.5, alternatively and from 0.1 to 0.4 in another embodiment.

The following OH$^-$:YO$_2$ molar ratios (with correction of trivalent element source) are useful lower OH$^-$:YO$_2$ molar ratio (with correction of trivalent element source) limits for these embodiments as disclosed in Table VI: 0.001, 0.002, 0.005, 0.01, 0.02, 0.05, 0.1, 0.2, 0.3, and 0.35. The following OH$^-$:YO$_2$ molar ratios (with correction of trivalent element source) are useful upper OH$^-$:YO$_2$ molar ratio (with correction of trivalent element source) limits for these embodiments as disclosed in Table VI: 0.39, 0.35, 0.31, 0.3, 0.2 and 0.1. The OH$^-$:YO$_2$ molar ratio (with correction of trivalent element source) ideally falls in a range between any one of the above-mentioned lower limits and any one of the above-mentioned upper limits, so long as the lower limit is less than or equal to the upper limit. The OH$^-$:YO$_2$ molar ratio (with correction of trivalent element source) may be present in an amount ranging from 0.001 to 0.39 in one embodiment, alternatively 0.01 to 0.35, alternatively 0.1 to 0.3, alternatively and from 0.1 to 0.25 in another embodiment.

The crystalline molecular sieve material of this disclosure may alternatively be prepared from a reaction mixture for hydrothermal reaction containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, the reaction mixture for hydrothermal reaction having a composition, in terms of mole ratios of oxides, within the following ranges in Table VII:

TABLE VII

| Reactants | Useful | Preferred |
|---|---|---|
| YO$_2$/X$_2$O$_3$ | 10 to infinity | 15-55 |
| H$_2$O/YO$_2$ | 1 to 10000 | 5-35 |
| OH$^-$/YO$_2$* | 0.64-2 | 0.7-2 |
| OH$^-$/YO$_2$** | 0.74-2 | 0.8-2 |
| M/YO$_2$ | 0.001-2 | 0.1-1 |
| R/YO$_2$ | 0.001-2 | 0.01-0.5 |
| Seed*** | 0-25 wt % | 1-5 wt % |
| R | Me$_6$-diquat-5 salt(s) | Me$_6$-diquat-5 salt(s) |

*The OH$^-$/YO$_2$ of this row is calculated with correction of trivalent element source.
**The OH$^-$/YO$_2$ of this row is calculated without correction of trivalent element source.
***The weight percent (wt %) of seed is based on the weight of the solid tetrahedral element oxide.

For these embodiments when reaction mixture for hydrothermal reaction having a composition as disclosed in Table VII, the OH$^-$/YO$_2$ molar ratio without correction of trivalent element source ranges from about 0.74 to about 2 and/or the OH$^-$/YO$_2$ molar ratio with correction of trivalent element source ranges from about 0.64 to about 2.

The following OH$^-$/YO$_2$ molar ratios (without correction of trivalent element source) are useful lower OH$^-$/YO$_2$ molar ratio (without correction of trivalent element source) limits for all disclosure processes: 0.74, 0.77, 0.78, 0.80, 0.90, 1 and 1.5. The following OH$^-$/YO$_2$ molar ratios (without correction of trivalent element source) are useful upper OH$^-$/YO$_2$ molar ratio (without correction of trivalent element source) limits for all disclosure processes: 2, 1.6, 1.4, 1.3, 1.2, 1, 0.9 and 0.8. The OH$^-$/YO$_2$ molar ratio (without correction of trivalent element source) ideally falls in a range between any one of the above-mentioned lower limits and any one of the above-mentioned upper limits, so long as the lower limit is less than or equal to the upper limit. The OH$^-$/YO$_2$ molar ratio (without correction of trivalent element source) may be present in an amount ranging from 0.74 to 2 in one embodiment, alternatively 0.8 to 2, alternatively 0.8 to 1, alternatively and from 0.8 to 1.1 in another embodiment.

The following OH$^-$/YO$_2$ molar ratios (with correction of trivalent element source) are useful lower OH$^-$/YO$_2$ molar ratio (with correction of trivalent element source) limits for all disclosure processes: 0.64, 0.65, 0.66, 0.7, 0.75, 0.80, 0.90, 1 and 1.5. The following OH$^-$/YO$_2$ molar ratios (with correction of trivalent element source) are useful upper OH$^-$/YO$_2$ molar ratio (with correction of trivalent element source) limits for all disclosure processes: 2, 1.6, 1.4, 1.3, 1.2, 1, 0.9 and 0.8. The OH$^-$/YO$_2$ molar ratio (with correction of trivalent element source) ideally falls in a range between any one of the above-mentioned lower limits and any one of the above-mentioned upper limits, so long as the lower limit is less than or equal to the upper limit. The OH$^-$/YO$_2$ molar ratio (with correction of trivalent element source) may be present in an amount ranging from 0.74 to 2 in one embodiment, alternatively 0.8 to 2, alternatively 0.8 to 1, alternatively and from 0.8 to 1.1 in another embodiment.

The crystalline molecular sieve material of this disclosure may alternatively be prepared from a reaction mixture for hydrothermal reaction containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, the reaction mixture for hydrothermal reaction having a composition, in terms of mole ratios of oxides, within the following ranges in Table VIII:

TABLE VIII

| Reactants | Useful | Preferred |
|---|---|---|
| $YO_2/X_2O_3$ | 10 to infinity | 15-55 |
| $H_2O/YO_2$ | 5-35 | 5-30 |
| $OH^-/YO_2$* | 0.001-2 | 0.001-2 |
| $M/YO_2$ | 0.001-2 | 0.1-1 |
| $R/YO_2$ | 0.001-2 | 0.01-0.5 |
| Seed** | 0-25 wt % | 1-5 wt % |
| R | $Me_6$-diquat-5 salt(s) | $Me_6$-diquat-5 salt(s) |

*The $OH^-/YO_2$ of this row is calculated with or witout correction of trivalent element source.
**The weight percent (wt %) of seed is based on the weight of the solid tetrahedral element oxide.

For these embodiments when reaction mixture for hydrothermal reaction having a composition as disclosed in Table VIII, the $H_2O:YO_2$ molar ratio ranges from about 5 to about 35 or from about 5 to 30. The following $H_2O:YO_2$ molar ratios are useful lower $H_2O:YO_2$ molar ratio limits for these embodiments as disclosed in Table VIII: 5, 10, 12, 15, 20, 22, 25 and 30. The following $H_2O:YO_2$ molar ratios are useful upper $H_2O:YO_2$ molar ratio limits for these embodiments as disclosed in Table VIII: 10, 15, 20, 25, 30 and 35. The $H_2O:YO_2$ molar ratio ideally falls in a range between any one of the above-mentioned lower limits and any one of the above-mentioned upper limits, so long as the lower limit is less than or equal to the upper limit. The $H_2O:YO_2$ molar ratio may be present in an amount ranging from 5 to 35 in one embodiment, alternatively 5 to 30, alternatively from 10 to 35, alternatively 10 to 30, alternatively 15 to 35, alternatively and from 15 to 30 in another embodiment.

The crystalline molecular sieve material of this disclosure may alternatively be prepared from a reaction mixture for hydrothermal reaction containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, the reaction mixture for hydrothermal reaction having a composition, in terms of mole ratios of oxides, within the following ranges in Table IX:

TABLE IX

| Reactants | Useful | Preferred |
|---|---|---|
| $YO_2/X_2O_3$ | 10 to infinity | 15-55 |
| $H_2O/YO_2$ | 1 to 10000 | 5-35 |
| $OH^-/YO_2$* | 0.001-2 | 0.001-2 |
| $M/YO_2$ | 0.001-2 | 0.1-1 |
| $R/YO_2$ | 0.001-2 | 0.01-0.5 |
| Seed** | 1 wppm - 25 wt % | 1-5 wt % |
| R | $Me_6$-diquat-5 salt(s) | $Me_6$-diquat-5 salt(s) |

*The $OH^-/YO_2$ of this row is calculated with or witout correction of trivalent element source.
**The weight percent (wt %) of seed is based on the weight of the solid tetrahedral element oxide.

For these embodiments when reaction mixture for hydrothermal reaction having a composition as disclosed in Table IX, the synthesis of the crystalline molecular sieve is facilitated by the presence of 1 wppm to about 25 wt %, preferably about 1 to about 5 wt %, seed crystals based on total weight of tetrahedral element oxide (e.g., silica) in the reaction mixture for hydrothermal reaction. The following seed crystals, in wt % based on total weight of tetrahedral element oxide of the reaction mixture for hydrothermal reaction, are useful lower seed crystals wt % limits for these embodiments as disclosed in Table IX: 0.01, 0.002, 0.005, 0.01, 0.02, 0.05, 0.1, 0.2, 0.5, 1, 2, 5, 10 and 15. The following seed crystals, in wt % based on total weight of tetrahedral element oxide of the reaction mixture for hydrothermal reaction, are useful upper seed crystals wt % limits for these embodiments as disclosed in Table IX: 1, 2, 5, 10, 15, 20 and 25. The seed crystals wt % ideally falls in a range between any one of the above-mentioned lower limits and any one of the above-mentioned upper limits, so long as the lower limit is less than or equal to the upper limit. The seed crystals, in wt % based on total weight of tetrahedral element oxide of the reaction mixture for hydrothermal reaction, may be present in an amount ranging from 0.01 to 25 in one embodiment, alternatively 0.01 to 20, alternatively from 0.1 to 10, alternatively 0.5 to 10, alternatively 0.5 to 5, alternatively and from 0.1 to 5 in another embodiment.

In some embodiments, Y comprises Ge and at least one non-germanium tetrahedral element (Y) which is same as Y except not including Ge. Sources of Ge include germanium oxide, germanium nitrate, and other germanium salts. The reaction mixture for hydrothermal reaction having a composition, in terms of mole ratios of oxides, within the following ranges in Table X:

TABLE X

| Reactants | Useful | Preferred |
|---|---|---|
| $(GeO_2 + YO_2)/X_2O_3$ | 10 to infinity | 15-600 |
| $H_2O/YO_2$ | 1 to 10000 | 1-35 |
| $OH^-/YO_2$* | 0.001-2 | 0.001-2 |
| $M/YO_2$ | 0.0-2 | 0.0-1 |
| $R/YO_2$ | 0.001-2 | 0.01-0.5 |
| Seed** | 0-25 wt % | 1-5 wt % |
| R | $Me_6$-diquat-5 OH and/or $Me_6$-diquat-6 OH | $Me_6$-diquat-5 OH |

*The $OH^-/YO_2$ of this row is calculated with or witout correction of trivalent element source.
**The weight percent (wt %) of seed is based on the weight of the solid tetrahedral element oxide.

For these embodiments when reaction mixture for hydrothermal reaction having a composition as disclosed in Table IX, the $(GeO_2+YO_2)/X_2O_3$ ranges from about 10 to about infinity or from about 15 to 600. The following $(GeO_2+YO_2)/X_2O_3$ molar ratios are useful lower $(GeO_2+YO_2)/X_2O_3$ molar ratio limits for these embodiments as disclosed in Table IX: 10, 12, 15, 20, 22, 25 and 30. The following $(GeO_2+YO_2)/X_2O_3$ molar ratios are useful upper $(GeO_2+YO_2)/X_2O_3$ molar ratio limits for these embodiments as disclosed in Table X: infinity, 5000, 1000, 600, 500 and 400. The $(GeO_2+YO_2)/X_2O_3$ molar ratio ideally falls in a range between any one of the above-mentioned lower limits and any one of the above-mentioned upper limits, so long as the lower limit is less than or equal to the upper limit. The $(GeO_2+YO_2)/X_2O_3$ molar ratio may be present in an amount ranging from 10 to infinity in one embodiment, alternatively 15 to 600, alternatively from 10 to 5000, alternatively 10 to 600, alternatively 15 to 500, alternatively and from 15 to 300 in another embodiment.

The sources of the various elements required in the final product may be any of those in commercial use or described in the literature, as may the method of preparation of the synthesis mixture.

Y is a tetravalent element selected from Groups 4-14 of the Periodic Table of the Elements, such as silicon and/or germanium, preferably silicon. In some embodiments of this disclosure, the source of $YO_2$ comprises solid $YO_2$, preferably about 30 wt % solid $YO_2$ in order to obtain the crystal product of this disclosure. When $YO_2$ is silica, the use of a silica source containing preferably about 30 wt % solid silica, e.g., silica sold by Degussa under the trade names Aerosil or Ultrasil (a precipitated, spray dried silica containing about 90 wt % silica), an aqueous colloidal suspension of silica, for example one sold by Grace Davison under the trade name Ludox, or HiSil (a precipitated hydrated $SiO_2$ containing about 87 wt % silica, about 6 wt % free $H_2O$ and about 4.5 wt % bound $H_2O$ of hydration and having a particle size of about 0.02 micron) favors crystal formation from the above mixture. Preferably, therefore, the $YO_2$, e.g., silica, source contains about 30 wt % solid $YO_2$, e.g., silica, and more preferably about 40 wt % solid $YO_2$, e.g., silica. The source of silicon may also be a silicate, e.g., an alkali metal silicate, or a tetraalkyl orthosilicate.

In additional embodiments of this disclosure, the source of $YO_2$ comprises acid of the tetravalent element (Y). When $YO_2$ is silica, the silica source may be silicic acid.

X is a trivalent element selected from Groups 3-13 of the Periodic Table of the Elements, such as aluminum, and/or boron, and/or iron and/or gallium, preferably aluminum. The source of $X_2O_3$, e.g., aluminum, is preferably aluminum sulphate, aluminum nitrate or hydrated alumina. Other aluminum sources include, for example, other water-soluble aluminum salts, sodium aluminate, or an alkoxide, e.g., aluminum isopropoxide, or aluminum metal, e.g., in the form of chips.

The alkali or alkali earth metal element is advantageously lithium, sodium, potassium, calcium, or magnesium. The source of alkali or alkali earth metal element is advantageously being metal oxide, metal chloride, metal fluoride, metal sulfate, metal nitrate, or metal aluminate. The sodium source advantageously being sodium hydroxide or sodium aluminate. The alkali metal may also be replaced by ammonium ($NH_4^+$) or its equivalents, e.g., alkyl-ammonium ion.

The $OH^-$:$YO_2$ molar ratio (without correction of trivalent element source) as used in this disclosure does not include correction of acid in the reaction mixture for hydrothermal reaction. It is calculated based on the total mole of hydroxide added to the reaction mixture for hydrothermal reaction divided by the total mole of Y element added to the reaction mixture for hydrothermal reaction. The hydroxide ($OH^-$) source is advantageously alkali metal oxide, e.g., $Li_2O$, $Na_2O$, $K_2O$, $Rb_2O$, $Cs_2O$, $Fr_2O$, or any combination thereof; alkali metal hydroxide, e.g., LiOH, NaOH, KOH, RbOH, CsOH, FrOH, or any combination thereof; ammonium hydroxide, alkali earth metal oxide, e.g., BeO, MgO, CaO, SrO, BaO, RaO, or any combination thereof; alkali earth metal hydroxide, e.g., $Be(OH)_2$, $Mg(OH)_2$, $Ca(OH)_2$, $Sr(OH)_2$, $Ba(OH)_2$, $Ra(OH)_2$, or any combination thereof; oxide(s) or hydroxide(s) of any element selected from Groups 3-17, and any combination thereof; and organic hydroxide(s), such as amine hydroxide(s), hydroxide of organic template (R) used in the synthesis.

The $OH^-$:$YO_2$ molar ratio (with correction of trivalent element source) as used in this disclosure include correction of acid in the reaction mixture for hydrothermal reaction. The mole of $OH^-$ after correction is calculated by subtracting three times the mole of trivalent element (if the trivalent element source is supplied in the form of salt other than oxide, hydroxide, or metal) from the total mole of hydroxide added to the reaction mixture for hydrothermal reaction. The $OH^-$:$YO_2$ molar ratio (with correction of trivalent element source) is, therefore, calculated based on the total mole of hydroxide after correction divided by the total mole of Y element added to the reaction mixture for hydrothermal reaction.

Directing agent R comprises at least one of N,N,N,N'N'N'-hexamethyl-1,5-hexanediaminium ($Me_6$-diquat-6) salt or N,N,N,N'N'N'-hexamethyl-1,5-pentanediaminium ($Me_6$-diquat-5) salt. Examples of $Me_6$-diquat-5 salt are hydroxide, chloride, bromide, fluoride, nitrate, sulfate, phosphate, or any mixture thereof. Examples of $Me_6$-diquat-6 salt are hydroxide, chloride, bromide, fluoride, nitrate, sulfate, phosphate, or any mixture thereof.

In some embodiment, the directing agent R comprises at least one of $Me_6$-diquat-5 dibromide, $Me_6$-diquat-5 dichloride, $Me_6$-diquat-5 difluoride, $Me_6$-diquat-5 diiodide, $Me_6$-diquat-5 dihydroxide, $Me_6$-diquat-5 sulfate, $Me_6$-diquat-5 dinitrate, $Me_6$-diquat-5 hydroxide bromide, $Me_6$-diquat-5 hydroxide chloride, $Me_6$-diquat-5 hydroxide fluoride, $Me_6$-diquat-5 hydroxide iodide, $Me_6$-diquat-5 hydroxide nitrate, $Me_6$-diquat-5 fluoride bromide, $Me_6$-diquat-5 fluoride chloride, $Me_6$-diquat-5 fluoride iodide, $Me_6$-diquat-5 fluoride nitrate, $Me_6$-diquat-5 chloride bromide, $Me_6$-diquat-5 chloride iodide, $Me_6$-diquat-5 chloride nitrate, $Me_6$-diquat-5 iodide bromide, $Me_6$-diquat-5 bromide nitrate, $Me_6$-diquat-6 dibromide, $Me_6$-diquat-6 dichloride, $Me_6$-diquat-6 difluoride, $Me_6$-diquat-6 diiodide, $Me_6$-diquat-6 dihydroxide, $Me_6$-diquat-6 sulfate, $Me_6$-diquat-6 dinitrate, $Me_6$-diquat-6 hydroxide bromide, $Me_6$-diquat-6 hydroxide chloride, $Me_6$-diquat-6 hydroxide fluoride, $Me_6$-diquat-6 hydroxide iodide, $Me_6$-diquat-6 hydroxide nitrate, $Me_6$-diquat-6 fluoride bromide, $Me_6$-diquat-6 fluoride chloride, $Me_6$-diquat-6 fluoride iodide, $Me_6$-diquat-6 fluoride nitrate, $Me_6$-diquat-6 chloride bromide, $Me_6$-diquat-6 chloride iodide, $Me_6$-diquat-6 chloride nitrate, $Me_6$-diquat-6 iodide bromide, $Me_6$-diquat-6 bromide nitrate, and any mixtures thereof.

A factor affecting the cost and the product quality of the synthesis of a crystalline molecular sieve is the amount of the directing agent (represented by the R:$YO_2$ molar ratio). The directing agent is generally the most expensive reactant(s) in the reaction mixture for hydrothermal reaction of many crystalline molecular sieves. The lower the amount of the directing agent in the reaction mixture for hydrothermal reaction (low R:$YO_2$ molar ratio), the cheaper the final molecular sieve produced.

For these embodiments as disclosed in Tables VI, VII, VIII and X, the reaction mixture for hydrothermal reaction may optionally contain seed crystals. It is well known that seeding a molecular sieve synthesis mixture frequently has beneficial effects, for example in controlling the particle size of the product, avoiding the need for an organic template, accelerating synthesis, and improving the proportion of product that is of the intended framework type. Usually the seeding crystals are from the synthesis similar to the one where they are used. In general any form of the crystalline material may be useful in facilitating synthesis on the new phase.

In some embodiments of this disclosure, for these embodiments as disclosed in Tables VI, VII, VIII, IX and optionally X, the M:$YO_2$ molar ratio ranges from about 0.001 to about 2.0. The following M:$YO_2$ molar ratios are useful lower M:$YO_2$ molar ratio limits for all disclosure processes: 0.001, 0.002, 0.005, 0.01, 0.02, 0.05, 0.1, 0.2, 0.5, 0.55, 0.76 and 1. The following M:$YO_2$ molar ratios are useful upper M:$YO_2$ molar ratio limits for all disclosure processes: 2, 1.5, 1.2, 1.1, 1, 0.9, 0.8, 0.59, 0.5, 0.4, 0.3, 0.2 and 0.1. The M:$YO_2$ molar ratio ideally falls in a range between any one of the above-mentioned lower limits and any one of the above-mentioned upper limits, so long as the lower limit is less than or equal to the upper limit. The M:$YO_2$ molar ratio may be present in an amount ranging from 0.001 to 0.59 in one embodiment, alternatively 0.01 to 0.5, alternatively from 0.74 to 2, alternatively 0.8 to 1, alternatively 0.001 to 2, alternatively and from 0.01 to 1 in another embodiment.

In some embodiments of this disclosure, for these embodiments as disclosed in Tables VI, VII, IX and X, the $H_2O$:$YO_2$ molar ratio ranges from about 1 to about 10000 or from about 1 to 35. The following $H_2O$:$YO_2$ molar ratios are useful lower $H_2O:YO_2$ molar ratio limits for all disclosure processes: 1, 2, 5, 10, 12, 15, 20, 22, 25, 30, 50, 100, 200, 500, 1000, 2000 and 5000. The following $H_2O:YO_2$ molar ratios are useful upper $H_2O:YO_2$ molar ratio limits for all disclosure processes: 2, 5, 10, 15, 20, 25, 30, 35, 50, 100, 200, 500, 1000, 2000, 5000 and 10000. The $H_2O:YO_2$ molar ratio ideally falls in a range between any one of the above-mentioned lower limits and any one of the above-mentioned upper limits, so long as the lower limit is less than or equal to the upper limit. The $H_2O:YO_2$ molar ratio may be present in an amount ranging from 1 to 35 in one embodiment, alternatively 5 to 35, alternatively from 1 to 10000, alternatively 1 to 5000, alternatively 5 to 1000, alternatively and from 10 to 100 in another embodiment.

In some embodiments of this disclosure, for these embodiments as disclosed in Tables VIII, IX and X, the $OH^-:YO_2$ molar ratio (with or without correction of trivalent element source) ranges from about 0.001 to about 2.0. The following $OH^-:YO_2$ molar ratios (with or without correction of trivalent element source) are useful lower $OH^-:YO_2$ molar ratio (with or without correction of trivalent element source) limits for all disclosure processes: 0.001, 0.002, 0.005, 0.01, 0.02, 0.05, 0.1, 0.2, 0.5, 0.55, 0.74 and 1. The following $OH^-:YO_2$ molar ratios (with or without correction of trivalent element source) are useful upper $OH^-:YO_2$ molar ratio (with or without correction of trivalent element source) limits for all disclosure processes: 2, 1.5, 1.2, 1.1, 1, 0.9, 0.8, 0.59, 0.5, 0.4, 0.3, 0.2 and 0.1. The $OH^-:YO_2$ molar ratio (with or without correction of trivalent element source) ideally falls in a range between any one of the above-mentioned lower limits and any one of the above-mentioned upper limits, so long as the lower limit is less than or equal to the upper limit. The $OH^-:YO_2$ molar ratio (with or without correction of trivalent element source) may be present in an amount ranging from 0.001 to 0.59 in one embodiment, alternatively 0.01 to 0.5, alternatively from 0.74 to 2, alternatively 0.8 to 1, alternatively 0.001 to 2, alternatively and from 0.01 to 1 in another embodiment.

In some embodiments of this disclosure, the $R:YO_2$ molar ratio ranges from about 0.001 to about 2.0. The following $R:YO_2$ molar ratios are useful lower $R:YO_2$ molar ratio limits for all disclosure processes: 0.001, 0.002, 0.005, 0.01, 0.02, 0.05, 0.1, 0.2, 0.5, 0.6, 0.7, 0.8, 0.9 and 1. The following $R:YO_2$ molar ratios are useful upper $R:YO_2$ molar ratio limits for all disclosure processes: 0.1, 0.2, 0.5, 0.6, 0.7, 0.8, 0.9, 1 and 2. The $R:YO_2$ molar ratio ideally falls in a range between any one of the above-mentioned lower limits and any one of the above-mentioned upper limits, so long as the lower limit is less than or equal to the upper limit. The $R:YO_2$ molar ratio may be present in an amount ranging from 0.001 to 2 in one embodiment, alternatively 0.01 to 1, alternatively from 0.1 to 2, alternatively 0.1 to 1, alternatively 0.1 to 0.5, alternatively and from 0.1 to 0.35 in another embodiment.

In some embodiments of this disclosure, the $YO_2/X_2O_3$ molar ratio for all disclosure processes ranges from about 10 to about infinity or from about 15 to 600. The following $YO_2/X_2O_3$ molar ratios are useful lower $YO_2/X_2O_3$ molar ratio limits for all disclosure processes: 10, 12, 15, 20, 22, 25 and 30. The following $YO_2/X_2O_3$ molar ratios are useful upper $YO_2/X_2O_3$ molar ratio limits for all disclosure processes: infinity, 5000, 1000, 600, 500, 400, 300, 200, 100, 90, 80, 70, 60, 50, 55, 40 and 30. The $YO_2/X_2O_3$ molar ratio ideally falls in a range between any one of the above-mentioned lower limits and any one of the above-mentioned upper limits, so long as the lower limit is less than or equal to the upper limit. The $YO_2/X_2O_3$ molar ratio may be present in an amount ranging from 10 to infinity in one embodiment, alternatively 15 to 600, alternatively from 10 to 5000, alternatively 10 to 600, alternatively 15 to 500, alternatively and from 15 to 55 in another embodiment.

In some embodiments of this disclosure, for these embodiments as disclosed in Tables VI, VII, VIII and X, the synthesis of the crystalline molecular sieve is facilitated by the presence of 0 to about 25 wt %, preferably about 1 to about 5 wt %, seed crystals based on total weight of tetrahedral element oxide (e.g., silica) of the reaction mixture for hydrothermal reaction. The following seed crystals, in wt % based on total weight of tetrahedral element oxide of the reaction mixture for hydrothermal reaction, are useful lower seed crystals wt % limits for all disclosure processes: 0.001, 0.002, 0.005, 0.01, 0.02, 0.05, 0.1, 0.2, 0.5, 1, 2, 5, 10 and 15. The following seed crystals, in wt % based on total weight of tetrahedral element oxide of the reaction mixture for hydrothermal reaction, are useful upper seed crystals wt % limits for all disclosure processes: 1, 2, 5, 10, 15, 20 and 25. The seed crystals wt % ideally falls in a range between any one of the above-mentioned lower limits and any one of the above-mentioned upper limits, so long as the lower limit is less than or equal to the upper limit. The seed crystals, in wt % based on total weight of tetrahedral element oxide of the reaction mixture for hydrothermal reaction, may be present in an amount ranging from 0.001 to 25 in one embodiment, alternatively 0.01 to 20, alternatively from 0.1 to 10, alternatively 0.5 to 10, alternatively 0.5 to 5, alternatively and from 0.1 to 5 in another embodiment.

After the crystallization of the reaction mixture for hydrothermal reaction is complete, the crystalline product may be recovered from the remainder of the reaction mixture for hydrothermal reaction, especially the liquid contents thereof. Such recovery may involve filtering the crystals and washing these crystals with water. However, in order to remove the entire undesired residue of the reaction mixture for hydrothermal reaction from the crystals, it is often necessary to subject the crystals to a high temperature calcination e.g., at 500° C., possibly in the presence of oxygen. Such a calcination treatment not only removes water from the crystals, but this treatment also serves to decompose and/or oxidize the residue of the organic directing agent which may be occluded in the pores of the crystals, possibly occupying ion exchange sites therein.

It should be realized that the reaction mixture for hydrothermal reaction components can be supplied by more than one source. The reaction mixture for hydrothermal reaction can be prepared either batchwise or continuously. Crystal size and crystallization time of the crystalline molecular sieve of this disclosure may vary with the nature of the reaction mixture for hydrothermal reaction employed and the crystallization conditions.

It will be understood by a person skilled in the art that the synthesis mixture having a composition within the molar ranges as discussed above means that the synthesis mixture is the product of mixing, adding, reacting, or by any means of providing such a mixture, wherein such product has a composition within the molar ranges as discussed above. The product of mixing, adding, reacting, or by any means of providing such a mixture may or may not contain individual ingredients when the synthesis mixture was prepared. The product of mixing, adding, reacting, or by any means of providing such a mixture, may even contain reaction product of individual ingredients when the synthesis mixture was prepared by mixing, adding, reacting, or by any means of providing such a mixture.

Crystallization Conditions

In some embodiments, when the reaction mixture for hydrothermal reaction containing neither Ge nor seed, crystallization of the crystalline molecular sieve of this disclosure can be carried out under crystallization conditions comprising temperature, time of crystallization, and agitation of at least 150 rotations per minute (RPM), preferably at least 200 RPM, more preferably at least 250 RPM. In some aspects for the reaction mixture for hydrothermal reaction containing neither Ge nor seed, the crystallization may be carried out with any type of agitation, e.g., stirring or rotating the vessel about a horizontal axis (tumbling). When the crystallization is carried out under agitation, the rate of the agitation is ranged from 150 to about 10000 RPM, preferably from 200 to about 5000 RPM. In other aspects for the reaction mixture for hydrothermal reaction containing neither Ge nor seed, the crystallization conditions have the following agitation rates that are useful agitation rate limits: 110, 120, 150, 200, 250, 300, 500, 1000, and 5000 and the following agitation rates that are useful upper agitation rate limits: 10000, 5000, 1000, 500 and 400. The agitation rate of the crystallization conditions, for a reaction mixture for hydrothermal reaction containing neither Ge nor seed, ideally falls in a range between any one of the above-mentioned lower limits and any one of the above-mentioned upper limits, so long as the lower limit is less than or equal to the upper limit. The agitation rate of the crystallization conditions may be present in an amount ranging from 150 to 10000 in one embodiment, alternatively 200 to 5000, alternatively from 200 to 1000, alternatively 240 to 500, alternatively 250 to 1000, alternatively and from 150 to 500 in another embodiment.

In some embodiments, when the reaction mixture for hydrothermal reaction containing Ge or seed, crystallization of the crystalline molecular sieve of this disclosure can be carried out under crystallization conditions comprising temperature, time of crystallization, and optionally agitation. In some aspects for the reaction mixture for hydrothermal reaction containing Ge or seed, the crystallization may be carried out at either static or stirred condition in a reactor vessel, such as for example, autoclaves. Optionally, the hydrothermal reaction is carried out with any type of agitation, e.g., stirring or rotating the vessel about a horizontal axis (tumbling). When the crystallization is carried out under agitation for the reaction mixture for hydrothermal reaction containing Ge or seed, the rate of the agitation is ranged from 1 to about 1000 RPM, preferably from 10 to about 400 RPM. In some embodiments, the crystallization conditions have the following agitation rates that are useful agitation rate limits for all disclosure processes: 1, 10, 20, 50, 100, 200 and 500 and the following agitation rates that are useful upper agitation rate limits for all disclosure processes: 100, 200, 500 and 1000. The agitation rate of the crystallization conditions ideally falls in a range between any one of the above-mentioned lower limits and any one of the above-mentioned upper limits, so long as the lower limit is less than or equal to the upper limit. The agitation rate of the crystallization conditions may be present in an amount ranging from 1 to 500 in one embodiment, alternatively 10 to 200, alternatively from 50 to 500, alternatively 20 to 500, alternatively 50 to 1000, alternatively and from 10 to 500 in another embodiment.

In some embodiments, the crystallization conditions have a temperature from about 100° C. to about 250° C. for a time sufficient for crystallization to occur at the temperature used, e.g., from about 1 hour to about 400 hours. Preferably, the crystallization conditions have a temperature from about 140° C. to about 180° C. for a time sufficient for crystallization to occur at the temperature used, e.g., from about 1 hour to about 200 hours.

In some embodiments of this disclosure, the crystallization conditions have the following temperatures that are useful temperature limits for all disclosure processes: 100, 110, 120, 130, 140, 150, 160, 170, 180, 190 and 200 and the following temperatures that are useful upper temperatures limits for all disclosure processes: 150, 160, 170, 180, 190, 200, 210, 220, 230, 240 and 250. The temperature of the crystallization conditions ideally falls in a range between any one of the above-mentioned lower limits and any one of the above-mentioned upper limits, so long as the lower limit is less than or equal to the upper limit. The temperature of the crystallization conditions may be present in an amount ranging from 100 to 250 in one embodiment, alternatively 100 to 200, alternatively from 140 to 200, alternatively 140 to 190, alternatively 140 to 180, alternatively and from 150 to 180 in another embodiment.

Thereafter, the crystals are separated from the liquid and recovered. The procedure may include an aging period, either at room temperature (~25° C.) or, preferably, at a moderately elevated temperature (less than 120° C.), before the hydrothermal treatment ("hydrothermal reaction") at more elevated temperature. The latter may include a period of gradual or stepwise variation in temperature.

The molecular sieve product from the synthesis may further be filtrated, washed with water, and/or dried. The crystalline molecular sieve formed by crystallization may be recovered and subjected for further treatment, such as, ion-exchange with ammonium salt(s) (e.g., ammonium hydroxide, ammonium nitrate, ammonium chloride, ammonium sulfate, ammonium phosphate, ammonium carbonate, or any combination thereof) and/or calcination in an oxidative atmosphere (e.g., air, gas with an oxygen partial pressure of greater than 0 kPa-a) at a temperature of greater than 200° C., preferably at least 300° C., more preferably at least 400° C., and most preferably at least 500° C.

Catalysis and Adsorption

A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known forming techniques, like spray drying, prilling, pelletizing and extrusion, have been and are being used to produce macrostructures in the form of, for example, spherical particles, extrudates, pellets and Tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

To the extent desired, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups 1-17, preferably Groups 2-12 of the Periodic Table of the Elements.

The crystalline molecular sieve of this disclosure, preferably the MCM-22 family molecular sieve, when employed either as an adsorbent or as a catalyst in an organic compound conversion process should be generally dehydrated, at least partially. This can be done by heating to a temperature in the range of e.g., 200° C. to 595° C. in an atmosphere such as air or nitrogen, and at atmospheric, sub-atmospheric or super-atmospheric pressures for e.g., between 30 minutes and 48 hours. The degree of dehydration is measured by the percentage of weight loss relative to the total weight loss of a molecular sieve sample at 595° C. under flowing dry nitrogen (less than 0.001 kPa partial pressure of water vapor) for 48 hours. Dehydration can also be performed at room temperature (~25° C.) merely by placing the silicate in a vacuum, but a longer time is required to obtain a sufficient amount of dehydration.

The crystalline molecular sieve of this disclosure especially in its metal, hydrogen and ammonium forms can be beneficially converted to another form by thermal treatment. This thermal treatment is generally performed by heating one of these forms at a temperature of at least 370° C. for at least 1 minute and generally not longer than 1000 hours. While sub-atmospheric pressure can be employed for the thermal treatment, atmospheric pressure is desired for reasons of convenience. The thermal treatment can be performed at a temperature up to about 925° C. The thermal treated product is particularly useful in the catalysis of certain hydrocarbon conversion reactions. The thermally treated product, especially in its metal, hydrogen and ammonium forms, is particularly useful in the catalysis of certain organic, e.g., hydrocarbon, conversion reactions. Non-limiting examples of such reactions include those described in U.S. Pat. Nos. 4,954,325; 4,973,784; 4,992,611; 4,956,514; 4,962,250; 4,982,033; 4,962,257; 4,962,256; 4,992,606; 4,954,663; 4,992,615; 4,983,276; 4,982,040; 4,962,239; 4,968,402; 5,000,839; 5,001,296; 4,986,894; 5,001,295; 5,001,283; 5,012,033; 5,019,670; 5,019,665; 5,019,664; and 5,013,422, each incorporated herein by reference as to the description of the catalytic reactions.

The crystalline molecular sieve of this disclosure can be shaped into a wide variety of particle sizes. Generally speaking, the particles can be in the form of a powder, a granule, or a molded product, such as an extrudate. In cases where the catalyst is molded, such as by extrusion, the crystals can be extruded before drying or partially dried and then extruded.

The crystalline molecular sieve of this disclosure may be used as an adsorbent, such as for separating at least one component from a mixture of components in the vapor or liquid phase having differential sorption characteristics with respect to the crystalline molecular sieve(s) of this disclosure. Therefore, at least one component can be partially or substantially totally separated from a mixture of components having differential sorption characteristics with respect to the crystalline molecular sieve(s) of this disclosure by contacting the mixture with the crystalline molecular sieve(s) of this disclosure to selectively sorb the one component.

The crystalline molecular sieve of this disclosure is useful as catalyst in a wide range of processes, including separation processes and hydrocarbon conversion processes. Specific examples of hydrocarbon conversion processes which are effectively catalyzed by the crystalline molecular sieve(s) of this disclosure by itself or in combination with one or more other catalytically active substances including other crystalline catalysts, include the following:

(i) alkylation of aromatic hydrocarbons, e.g., benzene, with long chain olefins, e.g., $C_{14}$ olefin, with reaction conditions including, individually or in any combination, a temperature of from about 340° C. to about 500° C., a pressure of from about 101 to about 20200 kPa-a (absolute), a weight hourly space velocity of from about 2 $hr^{-1}$ to about 2000 $hr^{-1}$ and an aromatic hydrocarbon/olefin mole ratio of from about 1/1 to about 20/1, to provide long chain alkyl aromatics which can be subsequently sulfonated to provide synthetic detergents;

(ii) alkylation of aromatic hydrocarbons with gaseous olefins to provide short chain alkyl aromatic compounds, e.g., the alkylation of benzene with propylene to provide cumene, with reaction conditions including, individually or in any combination, a temperature of from about 10° C. to about 125° C., a pressure of from about 101 to about 3030 kPa-a, and an aromatic hydrocarbon weight hourly space velocity (WHSV) of from 5 $hr^{-1}$ to about 50 $hr^{-1}$;

(iii) alkylation of reformate containing substantial quantities of benzene and toluene with fuel gas containing $C_5$ olefins to provide, inter alia, mono- and di-alkylates with reaction conditions including, individually or in any combination, a temperature of from about 315° C. to about 455° C., a pressure of from about 3000 to about 6000 kPa-a, a WHSV-olefin of from about 0.4 $hr^{-1}$ to about 0.8 $hr^{-1}$, a WHSV-reformate of from about 1 $hr^{-1}$ to about 2 $hr^{-1}$ and a gas recycle of from about 1.5 to 2.5 vol/vol fuel gas feed;

(iv) alkylation of aromatic hydrocarbons, e.g., benzene, toluene, xylene and naphthalene, with long chain olefins, e.g., $C_{14}$ olefin, to provide alkylated aromatic lube base stocks with reaction conditions including, individually or in any combination, a temperature of from about 160° C. to about 260° C. and a pressure of from about 2600 to 3500 kPa-a;

(v) alkylation of phenols with olefins or equivalent alcohols to provide long chain alkyl phenols with reaction conditions including, individually or in any combination, a temperature of from about 200° C. to about 250° C., a pressure of from about 1500 to 2300 kPa-a and a total WHSV of from about 2 $hr^{-1}$ to about 10 $hr^{-1}$;

(vi) conversion of light paraffins to olefins and aromatics with reaction conditions including, individually or in any combination, a temperature of from about 425° C. to about 760° C. and a pressure of from about 170 to about 15000 kPa-a;

(vii) conversion of light olefins to gasoline, distillate and lube range hydrocarbons with reaction conditions including, individually or in any combination, a temperature of from about 175° C. to about 375° C. and a pressure of from about 800 to about 15000 kPa-a;

(viii) two-stage hydrocracking for upgrading hydrocarbon streams having initial boiling points above about 260° C. to premium distillate and gasoline boiling range products in a first stage using the MCM-22 family molecular sieve of this disclosure in combination with a Groups 8-10 metal as catalyst with effluent therefrom being reaction in a second stage using zeolite Beta, also in combination with a Groups 8-10 metal, as catalyst, the reaction conditions including, individually or in any combination, a temperature of from about 340° C. to about 455° C., a pressure of from about 3000 to about 18000 kPa-a, a hydrogen circulation of from about 176 to about 1760 liter/liter and a liquid hourly space velocity (LHSV) of from about 0.1 to 10 $h^{-1}$;

(ix) a combination hydrocracking/dewaxing process in the presence of the MCM-22 family molecular sieve of this disclosure and a hydrogenation component as catalyst, or a mixture of such catalyst and zeolite Beta, with reaction conditions including, individually or in any combination, a temperature of from about 350° C. to about 400° C., a pressure of from about 10000 to about 11000 kPa-a, an LHSV of from about 0.4 to about 0.6 and a hydrogen circulation of from about 528 to about 880 liter/liter;

(x) reaction of alcohols with olefins to provide mixed ethers, e.g., the reaction of methanol with isobutene and/or isopentene to provide methyl-t-butyl ether (MTBE) and/or t-amyl methyl ether (TAM) with conversion conditions including, individually or in any combination, a temperature of from about 20° C. to about 200° C., a pressure of from 200 to about 20000 kPa-a, a WHSV (gram-olefin per hour gram-zeolite) of from about 0.1 hr$^{-1}$ to about 200 hr$^{-1}$ and an alcohol to olefin molar feed ratio of from about 0.1/1 to about 5/1;

(xi) toluene disproportionation with C$_9$+ aromatics as co-feed with reaction conditions including, individually or in any combination, a temperature of from about 315° C. to about 595° C., a pressure of from about 101 to about 7200 kPa-a, a hydrogen/hydrocarbon mole ratio of from about 0 (no added hydrogen) to about 10 and a WHSV of from about 0.1 hr$^{-1}$ to about 30 hr$^{-1}$;

(xii) preparation of the pharmaceutically-active compound 2-(4-isobutylphenyl) propionic acid, i.e. ibuprofen, by reacting isobutyl benzene with propylene oxide to provide the intermediate 2-(4-isobutylphenyl) propanol followed by oxidation of the alcohol to the corresponding carboxylic acid;

(xiii) use as an acid-binding agent in the reaction of amines with heterocyclic fiber-reactive components in preparation of dyes to prepare practically salt-free reactive dye-containing solution, as in German Patent No. DE 3,625, 693, incorporated entirely herein by reference;

(xiv) as the absorbent for separating 2,6-toluene diisocyanate (2,6-TDI) from isomers if TDI as in U.S. Pat. No. 4,721,807, incorporated entirely herein by reference, whereby a feed mixture comprising 2,6-TDI and 2,4-TDI is contacted with the present MCM-22 family molecular sieve which has been cation-exchanged with K ions to absorb the 2,6-TDI, followed by recovering the 2,6-TDI by desorption with desorbent material comprising toluene;

(xv) as the absorbent for separating 2,4-TDI from its isomers as in U.S. Pat. No. 4,721,806, incorporated entirely herein by reference, whereby a feed mixture comprising 2,4-TDI and 2,6-TDI is contact with the present MCM-22 family molecular sieve which has been cation-exchanged with Na, Ca Li and/or Mg ions to absorb the 2,4-TDI, followed by recovering the 2,4-TDI by desorption with desorbent material comprising toluene;

(xvi) in a process for decreasing the durene content of a 90-200° C.+ bottoms fraction obtained from the catalytic conversion of methanol to gasoline which comprises contacting the durene-containing bottoms fraction with hydrogen over a catalyst of the present MCM-22 family molecular sieve with a hydrogenation metal, at conditions including, individually or in any combination, a temperature of from about 230° C. to about 425° C. and a pressure of from about 457 to about 22000 kPa-a;

(xvii) in a processes for co-producing phenol and ketones that proceed through benzene alkylation, followed by formation of the alkylbenzene hydroperoxide and cleavage of the alkylbenzene hydroperoxide into phenol and ketone, e.g., benzene and propylene to phenol and acetone, benzene and C$_4$ olefins to phenol and methyl ethyl ketone, such as those described for example in international application PCT/EP2005/008557, which can be followed by conversion of phenol and acetone to bis-phenol-A as described in international application PCT/EP2005/008554, benzene to phenol and cyclohexanone, or benzene and ethylene to phenol and methyl ethyl ketone, as described for example in PCT/EP2005/008551;

(xviii) in a process of benzene alkylation reactions where selectivity to the monoalkylbenzene is required, e.g., selectively sec-butylbenzene from benzene and C$_4$ olefin feeds that are rich in linear butenes, as described in international application PCT/EP2005/008557, preferably, this conversion is carried out by co-feeding benzene and the C$_4$ olefin feed with the catalyst of the present invention, at a temperature of about 60° C. to about 260° C., for example of about 100° C. to 200° C., a pressure of 7000 kPa-a or less, and a feed weight hourly space velocity (WHSV) based on C$_4$ alkylating agent of from about 0.1 to 50 h$^{-1}$ and a molar ratio of benzene to C$_4$ alkylating agent from about 1 to about 50; and (xix) in a process for transalkylations, such as, for example, polyalkylbenzene transalkylations.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. The materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline molecular sieve and inorganic oxide matrix vary widely, with the crystal content ranging from about 1 to about 99 percent by weight and more usually, particularly when the composite is prepared in the form of beads, in the range of about 20 to about 80 wt % of the composite.

The following examples reflect embodiments of the invention and are by no means intended to be limiting of the scope of the invention.

EXAMPLES

Examples 1, 1A (Comparative) and 2

Reaction mixtures for hydrothermal reaction were prepared from water, Me$_6$-diquat-5 ("R") dibromide (SACHEM, Inc.), silica (Ultrasil™, Degussa Corp.), aluminum sulfate solution (8.1 wt % Al$_2$O$_3$) solution, and 50 wt % sodium hydroxide solution. The mixtures had the following molar compositions as shown in Table IX:

TABLE IX

|  | Example 1 | Example 1A | Example 2 |
| --- | --- | --- | --- |
| SiO$_2$/Al$_2$O$_3$ | 23.6 | 23.6 | 25.5 |
| H$_2$O/SiO$_2$ | 21 | 21 | 20 |
| OH$^-$/SiO$_2$* | 0.22 | 0.26 | 0.24 |
| OH$^-$/SiO$_2$** | 0.47 | 0.51 | 0.48 |
| Na$^+$/SiO$_2$ | 0.47 | 0.51 | 0.48 |
| R/SiO$_2$ | 0.15 | 0.15 | 0.14 |
| Temperature (° C.) | 170 | 170 | 170 |
| Stirring speed (RPM) | 250 | 100 | 250 |
| Seed (wt %) | 0 | 0 | 0 |
| Time (hr) | 80, 92 | 72 | 80 |
| XRD Result | This invention (80 hrs) (See FIG. 1a); this invention and <5% EUO zeolite (92 hrs) (See FIG. 1b) | EMM-10-P and <5% Analcine (See FIG. 2) | This invention (See FIG. 4) |
| SiO$_2$/Al$_2$O$_3$ (molar ratio) | 21 | 19.5 | 21 |
| BET area (m$^2$/g) | 522 (87 external) |  | 506 (109 external) |
| Hexane cracking (ALPHA) | 260 |  |  |
| Morphology |  | 5-20 micron spherical (round, oval) aggregates of intergrown platelet crystals of less than 0.1 micron thickness (See FIG. 3) | 5-20 micron spherical (round, oval) aggregates of intergrown platelet crystals of less than 0.1 micron thickness (See FIG. 5) |
| Crystal size (SEM) | NA | 5-20 micron (See FIG. 3) | 5-20 micron (See FIG. 5) |
| Thickness (SEM) | NA | Less than 0.1 micron (See FIG. 3) | Less than 0.1 micron (See FIG. 5) |

*The OH$^-$/SiO$_2$ of this row is calculated with correction of trivalent element source.
**The OH$^-$/SiO$_2$ of this row is calculated without correction of trivalent element source.

The mixtures of the above Examples were crystallized at 170° C. in a Parr autoclave with stirring. After crystallization, the reaction mixture for hydrothermal reaction slurries were filtered, washed with water and dried in air at 120° C.

The XRD of Example 1 at 80 hours (FIG. 1a) shows the following features:

(1) d-spacing maximum at 12.33±0.23 Angstroms;
(2) d-spacing maximum between 14.17 and 12.57 Angstroms; and
(3) a non-discrete d-spacing maximum between 8.8 and 11.1 Angstroms, wherein the peak intensity of the d-spacing maximum between 14.17 and 12.57 Angstroms is less than 90% of the peak intensity of the d-spacing maximum at 12.33±0.23 Angstroms.

The XRD of Example 1 at 80 hours (FIG. 1a) also shows the following peaks which are common features of the MCM-22 molecular sieves as listed in Table X:

TABLE X

| Interplanar d-Spacing (Å) | Relative Intensity, I/I$_o$ × 100 |
| --- | --- |
| 4.41 ± 0.1 | W-M, broad |
| 3.96 ± 0.08 | W-VS, broad |

TABLE X-continued

| Interplanar d-Spacing (Å) | Relative Intensity, I/I$_o$ × 100 |
| --- | --- |
| 3.57 ± 0.06 | W-M |
| 3.43 ± 0.06 | M-VS |

The XRD of Example 1 at 92 hours (FIG. 1b) shows the same feature of FIG. 1a together with about less than 5% EUO zeolite. The XRD of Example 2 (FIG. 5) shows the same feature of FIG. 1 with less than 5% analcine.

The XRD of Example 1A shows the same feature of EMM-10-P.

Example 3 (Seed for Example 4)

The reaction mixture was made according to the following procedure. To a reactor was added 376.2 g of water and 75.9 g of Al$_2$(SO$_4$)$_3$.18H$_2$O (Riedel-de Haen). To this solution was added 62.1 g of a 50 wt % solution of NaOH, the NaOH used was from Baker. Then 91.1 g of Ultrasil VN 35P (Ultrasil Corporation) was added and mixed in the solution, followed by the addition of 145.8 g of a 50 wt % solution of pentamethonium dibromide (SACHEM Inc.). The mixture was stirred until homogeneous. The molar composition of the reaction mixture can be expressed as:

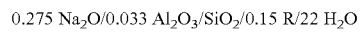

0.275 Na$_2$O/0.033 Al$_2$O$_3$/SiO$_2$/0.15 R/22 H$_2$O

The reactor was closed, stirred and heated with a rate of 25° C./hr to 170° C. Heating was continued under stirred conditions for 72 hr. After cooling to room temperature, the crystals were recovered from the mother liquor by centrifuging and washed 3 times with water. The washed crystals were dried overnight at 120° C. The yield of the crystals was 8.8 wt % relative to the total amount of the starting synthesis mixture. XRD and SEM are attached in the figures (FIGS. 6 and 7).

|  | Example 3 |
| --- | --- |
| $SiO_2/Al_2O_3$ | 33 |
| $H_2O/SiO_2$ | 22 |
| $OH^-/SiO_2$* | 0.35 |
| $OH^-/SiO_2$** | 0.55 |
| $Na^+/SiO_2$ | 0.55 |
| $R/SiO_2$ | 0.15 |
| Temperature (° C.) | 170 |
| Stirring speed (RPM) | 100 |
| Seed (wt %) | none |
| Crystallization Time (hr) | 72 |
| XRD Pattern | See FIG. 6 |
| $SiO_2/Al_2O_3$ (molar ratio) | n.a. |
| BET area (m²/g) | n.a. |
| Hexane cracking (ALPHA) | n.a. |
| Morphology (SEM) | Flakes (See FIG. 7) |
| Crystal size (SEM) | Estimated Largest diameter less than 2 μm (See FIG. 7) |
| Thickness (SEM) | ~100 nm (See FIG. 7) |

*The $OH^-/SiO_2$ of this row is calculated with correction of trivalent element source.
**The $OH^-/SiO_2$ of this row is calculated without correction of trivalent element source.

The XRD of Example 3 (FIG. 6) shows the following features same as FIG. 1:

(1) d-spacing maximum at 12.33±0.23 Angstroms;
(2) d-spacing maximum between 14.17 and 12.57 Angstroms; and
(3) a non-discrete d-spacing maximum between 8.8 and 11.1 Angstroms, wherein the peak intensity of the d-spacing maximum between 14.17 and 12.57 Angstroms is less than 90% of the peak intensity of the d-spacing maximum at 12.33±0.23 Angstroms.

The XRD of Example 3 (FIG. 6) also shows the following peaks which are common features of the MCM-22 molecular sieves as listed in Table X.

Example 4

The reaction mixture was made according to the following procedure. To a Teflon reactor liner was added a water based solution of sodium aluminate (containing 10 wt % of NaOH and 7.8 wt % of $Al_2O_3$, the NaOH used was from Baker, the aluminumhydroxide from Alcoa). To this solution was added a 40 wt % sodium hydroxide solution (NaOH from Baker). While stirring, Ultrasil VN 35P (Ultrasil Corporation) was added and mixed in the solution. Then a 50 wt % solution of pentamethonium dibromide (SACHEM Inc.) was added. After the mixture was homogenized, crystals from Example 3 were added to obtain a concentration of 0.5 wt % relative to the total weight of the synthesis mixture. The quantities used in the above mixture were such that the molar composition of the reaction mixture can be expressed as:

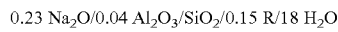
0.23 $Na_2O$/0.04 $Al_2O_3$/$SiO_2$/0.15 R/18 $H_2O$

The liner was than placed in a stirred reactor which was closed and heated with a rate of 25° C./hr to 170° C. Heating was continued under stirred conditions for 60 hr. After cooling to room temperature, the crystals were recovered from the mother liquor by centrifuging and washed 4 times with water. The washed crystals were dried overnight at 120° C. The yield of the crystals was 13.9 wt % relative to the total amount of the starting synthesis mixture. XRD and SEM are attached in the figures (FIGS. 8 and 9).

|  | Example 4 |
| --- | --- |
| $SiO_2/Al_2O_3$ | 25 |
| $H_2O/SiO_2$ | 18 |
| $OH^-/SiO_2$* | 0.76 |
| $Na^+/SiO_2$ | 0.46 |
| $R/SiO_2$ | 0.15 |
| Temperature (° C.) | 170 |
| Stirring speed (RPM) | 60 |
| Seed (wt %) | 0.5 |
| Crystallization Time (hr) | 60 |
| XRD Pattern | See FIG. 8 |
| $SiO_2/Al_2O_3$ (molar ratio) | n.a. |
| BET area (m²/g) | n.a. |
| Hexane cracking (ALPHA) | n.a. |
| Morphology (SEM) | Flakes (See FIG. 9) |
| Crystal size (SEM) | Estimated Largest diameter less than 2 μm (See FIG. 9) |
| Thickness (SEM) | ~100 nm (See FIG. 9) |

*The $OH^-/SiO_2$ of this row is calculated with correction of trivalent element source since aluminum was suplied as $Al_2O_3$.

The XRD of Example 3 (FIG. 8) shows the following features as FIG. 1:

(1) d-spacing maximum at 12.33±0.23 Angstroms;
(2) d-spacing maximum between 14.17 and 12.57 Angstroms; and
(3) a non-discrete d-spacing maximum between 8.8 and 11.1 Angstroms, wherein the peak intensity of the d-spacing maximum between 14.17 and 12.57 Angstroms is less than 90% of the peak intensity of the d-spacing maximum at 12.33±0.23 Angstroms.

The XRD of Example 4 (FIG. 8) also shows the following peaks which are common features of the MCM-22 molecular sieves as listed in Table X.

Example 5

The reaction mixture was made according to the following procedure. To a stainless steel autoclave was added 28.7 g of a 22% water based solution of hexamethonium hydroxide [R] (SACHEM, Inc.). While this solution was stirred, 1.8 g of germanium oxide (99.99 wt %, Aldrich) was added and the mixture was homogenized before 18.5 g of tetraethylorthosilicate (98 wt %, Aldrich) was added. To this mixture 1.1 g of aluminumisopropoxide (98 wt %, Aldrich) was added. While stirring, the homogeneous mixture was heated to 60° C. After heating for 1 hr the stirring was stopped and heating continued for another 1.5 hr under static conditions. After cooling to room temperature 9.5 g of the initial mixture was evaporated during the reaction. The overall molar composition of the synthesis mixture prior to heating can be expressed as:

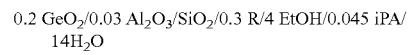
0.2 $GeO_2$/0.03 $Al_2O_3$/$SiO_2$/0.3 R/4 EtOH/0.045 iPA/ 14$H_2O$

After this pre-treatment the autoclave was closed and heated without agitation with a rate of 20° C./hr to 190° C. Heating was continued under static conditions for 144 hr. After cooling to room temperature, the crystals were recovered from the mother liquor by centrifuging and washed 4 times with 150 ml of water. The washed crystals were dried overnight at 120° C. The yield of the crystals was 14 wt % relative to the total amount of the starting synthesis mixture. XRD and SEM are attached in the figures (FIGS. 10 and 11).

|  | Example 5 |
| --- | --- |
| $SiO_2/Al_2O_3$ | 33 |
| $(GeO_2 + SiO_2)/Al_2O_3$ | 40 |
| $H_2O/SiO_2$ | 14 |
| $H_2O/(GeO_2 + SiO_2)$ | 11.7 |
| $OH^-/SiO_2$* | 0.3 |
| $OH^-/(GeO_2 + SiO_2)$* | 0.25 |
| $R/SiO_2$ | 0.3 |
| Temperature (° C.) | 190 |
| Stirring speed (RPM) | 0 |
| Seed (wt %) | none |
| Crystallization Time (hr) | 144 |
| XRD Pattern | FIG. 10 |
| $SiO_2/Al_2O_3$ (molar ratio) | n.a. |
| BET area (m²/g) | n.a. |
| Hexane cracking (ALPHA) | n.a. |
| Morphology | Flake (See FIG. 11) |
| Crystal size (SEM) | Estimated Largest diameter less than 2 μm (See FIG. 11) |
| Thickness (SEM) | ~100 nm (See FIG. 11) |

*The $OH^-/SiO_2$ and $OH^-/(GeO_2 + SiO_2)$ of these rows are calculated without correction of trivalent element source since aluminum was supplied as aluminumisopropoxide.

The XRD of Example 5 (FIG. 10) shows the following features as FIG. 1:

(1) d-spacing maximum at 12.33±0.23 Angstroms;
(2) d-spacing maximum between 14.17 and 12.57 Angstroms; and
(3) a non-discrete d-spacing maximum between 8.8 and 11.1 Angstroms, wherein the peak intensity of the d-spacing maximum between 14.17 and 12.57 Angstroms is less than 90% of the peak intensity of the d-spacing maximum at 12.33±0.23 Angstroms.

The XRD of Example 5 (FIG. 10) also shows peaks which are common features of the MCM-22 molecular sieves as listed in Table X.

All patents and patent applications, test procedures (such as ASTM methods), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

The meanings of terms used herein shall take their ordinary meaning in the art; reference shall be taken, in particular, to Handbook of Petroleum Refining Processes, Third Edition, Robert A. Meyers, Editor, McGraw-Hill (2004). In addition, all patents and patent applications, test procedures (such as ASTM methods), and other documents cited herein are fully incorporated by reference to the extent such disclosure is not inconsistent with this invention and for all jurisdictions in which such incorporation is permitted. Also, when numerical lower limits and numerical upper limits are listed herein, ranges from any lower limit to any upper limit are contemplated. Note further that Trade Names used herein are indicated by a ™ symbol or ® symbol, indicating that the names may be protected by certain trademark rights, e.g., they may be registered trademarks in various jurisdictions.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A crystalline MCM-22 family molecular sieve having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11. Angstroms, wherein the peak intensity of the d-spacing maximum between 12.57 to about 14.17 Angstroms is less than 90% of the peak intensity of the d-spacing maximum at 12.33±0.23 Angstroms.

2. The crystalline MCM-22 family molecular sieve of claim 1, further comprising XRD peaks at d-spacing maxima at 3.57±0.06 and 3.43±0.06 Angstroms.

3. The crystalline molecular sieve of claim 2, wherein the X-ray diffraction pattern further includes a d-spacing maximum at 28±1 Angstroms.

4. The crystalline molecular sieve recited in claim 3, wherein the X-ray diffraction pattern includes values and relative intensities substantially as shown in the follow Table:

| Interplanar d-Spacing (Å) | Relative Intensity, $I/I_o \times 100$ |
| --- | --- |
| 14.17 > d > 12.57 | M-VS |
| 12.33 ± 0.23 | M-VS |
| 11.1 to 8.8 | W-S |
| 3.57 ± 0.06 | W-M |
| 3.43 ± 0.06 | M-VS. |

5. The crystalline molecular sieve recited in claim 2, wherein the X-ray diffraction pattern includes values and relative intensities substantially as shown in the follow Table:

| Interplanar d-Spacing (Å) | Relative Intensity, $I/I_o \times 100$ |
| --- | --- |
| 14.17 > d > 12.57 | M-VS |
| 12.33 ± 0.23 | M-VS |
| 11.1 to 8.8 | W-S |
| 3.57 ± 0.06 | W-M |
| 3.43 ± 0.06 | M-VS. |

6. The crystalline molecular sieve recited in claim 2, further comprising XRD peaks at d-spacing maximum at 4.41±0.1 Angstroms.

7. The crystalline molecular sieve recited in claim 6, wherein the X-ray diffraction pattern includes values and relative intensities substantially as shown in the follow Table:

| Interplanar d-Spacing (Å) | Relative Intensity, $I/I_o \times 100$ |
| --- | --- |
| 14.17 > d > 12.57 | M-VS |
| 12.33 ± 0.23 | M-VS |
| 11.1 to 8.8 | W-S |
| 4.41 ± 0.1 | W-M, broad |
| 3.96 ± 0.08 | W-VS, broad |
| 3.57 ± 0.06 | W-M |
| 3.43 ± 0.06 | M-VS. |

8. The crystalline molecular sieve of claim 1, wherein the X-ray diffraction pattern further includes a d-spacing maximum at 28±1 Angstroms.

9. The crystalline molecular sieve recited in claim 8, wherein the X-ray diffraction pattern includes values and relative intensities substantially as shown in the follow Table:

| Interplanar d-Spacing (Å) | Relative Intensity, $I/I_o \times 100$ |
|---|---|
| 14.17 > d > 12.57 | M-VS |
| 12.33 ± 0.23 | M-VS |
| 11.1 to 8.8 | W-S |
| 3.57 ± 0.06 | W-M |
| 3.43 ± 0.06 | M-VS. |

10. The crystalline molecular sieve recited in claim 8, further comprising XRD peaks at d-spacing maximum at 4.41±0.1 Angstroms.

11. The crystalline molecular sieve recited in claim 10, wherein the X-ray diffraction pattern includes values and relative intensities substantially as shown in the follow Table:

| Interplanar d-Spacing (Å) | Relative Intensity, $I/I_o \times 100$ |
|---|---|
| 14.17 > d > 12.57 | M-VS |
| 12.33 ± 0.23 | M-VS |
| 11.1 to 8.8 | W-S |
| 4.41 ± 0.1 | W-M, broad |
| 3.96 ± 0.08 | W-VS, broad |
| 3.57 ± 0.06 | W-M |
| 3.43 ± 0.06 | M-VS. |

12. A crystalline molecular sieve made by the steps of:
(a) providing a mixture comprising at least one source of at least one tetravalent element (Y), at least one source of at least one alkali or alkali earth metal element, at least one directing-agent (R), water, and optionally at least one source of at least one trivalent element (X), said mixture having the following molar ratio:
$Y:X_2$=10 to infinity
$H_2O:Y$=1 to 10000
$OH^-:Y$=0.001 to 0.59
$M^+:Y$=0.001 to 2
$R:Y$=0.001 to 2
wherein M is an alkali metal and R is at least one N,N,N,N'N'N'-hexamethyl-1,5pentanediaminium salt(s), N,N,N,N'N'N'-hexamethyl-1,6-hexanediaminium salt(s), or any combination thereof, wherein said $OH^-:Y$ is calculated without trivalent element source correction; and
(b) submitting the mixture at crystallization conditions to form a product comprising the desired crystalline molecular sieve, wherein the crystallization conditions comprise a temperature in the range of from 100° C. to 250° C., a stirring speed of ranging from at least 150 RPM to less than 5000 RPM, and a crystallization time from about 1 hour to 400 hours; and
(c) recovering the crystalline molecular sieve.

13. The crystalline molecular sieve of claim 12, wherein the $OH^-:Y$ without trivalent element correction ranges from 0.01 to 0.5.

14. The crystalline molecular sieve of claim 12, further comprising $OH^-:Y$ with trivalent element correction ranges of from 0.01 to 0.39.

15. The method of claim 12, wherein the $H_2O:Y$ molar ratio is in the range of from 5 to 35.

16. A crystalline molecular sieve made by the method comprising the steps of:
(a) providing a mixture comprising at least one source of at least one tetravalent element (Y), at least one source of at least one alkali or alkali earth metal element, at least one directing-agent (R), water, and optionally at least one source of at least one trivalent element (X), said mixture having the following molar ratio:
$Y:X_2$=10 to infinity
$H_2O:Y$=1 to 10000
$OH^-:Y$=0.74 to 2
$M^+:Y$=0.001 to 2
$R:Y$=0.001 to 2
wherein M is an alkali metal and R is at least one N,N,N,N'N'N'-hexamethyl-1,5-pentanediaminium salt(s), N,N,N,N'N'N'-hexamethyl-1,6-hexanediaminium salt(s), or any combination thereof, wherein said $OH^-:Y$ is calculated without trivalent element source correction; and
(b) submitting the mixture at crystallization conditions to form a product comprising the desired crystalline molecular sieve, wherein the crystallization conditions comprise a temperature in the range of from 100° C. to 200° C., a stirring speed of ranging from at least 150 RPM to less than 5000 RPM, and a crystallization time from about 1 hour to 400 hours; and
(c) recovering the crystalline molecular sieve.

17. The crystalline molecular sieve of claim 16, wherein the $OH^-:Y$ is in the range of from 0.8 to 1.

18. The crystalline molecular sieve of claim 16, further comprising $OH^-:Y$ with trivalent element correction ranges of from 0.64 to 2.

19. The crystalline molecular sieve of claim 18, wherein the $H_2O:Y$ molar ratio is in the range of from 5 to 35.

20. A crystalline molecular sieve made by the method comprising the steps of:
(a) providing a mixture comprising at least one source of at least one tetravalent element (Y), at least one source of at least one alkali or alkali earth metal element, at least one directing-agent (R), water, and optionally at least one source of at least one trivalent element (X), said mixture having the following molar ratio:
$Y:X_2$=10 to infinity
$H_2O:Y$=5 to 35
$OH^-:Y$=0.001 to 2
$M^+:Y$=0.001 to 2
$R:Y$=0.001 to 2
wherein M is an alkali metal and R is at least one N,N,N,N'N'N'-hexamethyl-1,5-pentanediaminium salt(s), N,N,N,N'N'N'-hexamethyl-1,6-hexanediaminium salt(s), or any combination thereof, wherein said $OH^-:Y$ is calculated with or without trivalent element source correction; and
(b) submitting the mixture at crystallization conditions to form a product comprising the desired crystalline molecular sieve, wherein the crystallization conditions comprise a temperature in the range of from 100° C. to 200° C., a stirring speed of ranging from at least 150 RPM to less than 5000 RPM, and a crystallization time from about 1 hour to 400 hours; and
(c) recovering the crystalline molecular sieve.

21. The crystalline molecular sieve of claim 20 wherein the $Y:X_2$ is in the range of from 10 to 55.

22. The crystalline molecular sieve of claim 20 wherein the crystallization conditions further comprise a stirring, said stirring has a speed in the range of from 200 to 1000 RPM.

23. The crystalline molecular sieve of claim 20, any one of claims wherein the R:Y is in the range of from 0.01 to 0.5.

24. A crystalline molecular sieve made by the method comprising the steps of:
   (a) providing a mixture comprising at least one source of at least one tetravalent element (Y), at least one source of at least one alkali or alkali earth metal element, at least one directing-agent (R), water, at least one seed, and optionally at least one source of at least one trivalent element (X), said mixture having the following molar ratio:
   $Y:X_2=10$ to infinity
   $H_2O:Y=1$ to 10000
   $OH^-:Y=0.001$ to 2
   $M^+:Y=0.001$ to 2
   $R:Y=0.001$ to 2
   wherein M is an alkali metal and R is at least one N,N,N,N'N'N'-hexamethyl-1,5-pentanediaminium salt(s), N,N,N,N'N'N'-hexamethyl-1,6-hexanediaminium salt(s), or any combination thereof, wherein said $OH^-:Y$ is calculated with or without trivalent element source correction, wherein said seed has a concentration in said mixture ranging from about 0.01 to 10 wt% based on the weight of said tetravalent element oxide in said mixture; and
   (b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours; and
   (c) recovering the crystalline molecular sieve.

25. The crystalline molecular sieve of claim 24, said seed has a concentration in said mixture ranging from about 0.1 to 5 wt% based on the weight of said tetravalent element oxide in said mixture.

26. The crystalline molecular sieve of claim 24 having the structure of an MCM-22 family molecular sieve.

27. A crystalline molecular sieve made by the method comprising the steps of:
   (a) providing a mixture comprising at least one source of at least one non- germanium tetravalent element (Y), at least one source of germanium (Ge), at least one directing-agent (R), water, and optionally at least one source of at least one trivalent element (X) and at least one source of at least one alkali or alkali earth metal element, said mixture having the following molar ratio:
   $(Ge+Y):X_2=10$ to infinity
   $H_2O:Y=1$ to 10000
   $M^+:Y=0$ to 2
   $R:Y=0.001$ to 2
   wherein M is an alkali metal and R is at least one N,N,N,N'N'N'-hexamethyl-1,5-pentanediaminium salt(s), N,N,N,N'N'N'hexamethyl-1,6-hexanediaminium salt(s), or any combination thereof; and
   (b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours; and
   (c) recovering the crystalline molecular sieve.

28. The crystalline molecular sieve of claim 27, wherein said $(Ge+Y):X_2$ is in the range of from 15-600.

29. The crystalline molecular sieve of claim 27, wherein said $H_2O:Y$ is in the range of from 5-35.

30. The crystalline molecular sieve of claim 27, wherein said M+:Y is in the range of from 0-1.

31. The crystalline molecular sieve of claim 27, wherein the crystallization conditions further comprise a stirring, said stirring has a speed in the range of from 50 to 1000 RPM.

32. The crystalline molecular sieve of claim 27, wherein the tetravalent element (Y) is silicon.

33. The crystalline molecular sieve of claim 27, wherein the trivalent element (X) is aluminum.

34. The crystalline molecular sieve of claim 27 having the structure of an MCM-22 family molecular sieve.

35. A process for hydrocarbon conversion, comprising the step of:
   (a) contacting a hydrocarbon feedstock with the crystalline molecular sieve made by the method of in any one of claims 12, 16, 20, 24 and 27, under conversion conditions to form a product.

* * * * *